United States Patent
Lansdorp et al.

(10) Patent No.: US 12,227,794 B2
(45) Date of Patent: Feb. 18, 2025

(54) METHOD FOR PARENT-OF-ORIGIN DISEASE ALLELE DETECTION FOR THE DIAGNOSIS AND MANAGEMENT OF GENETIC DISEASES

(71) Applicant: PROVINCIAL HEALTH SERVICES AUTHORITY, Vancouver (CA)

(72) Inventors: Peter Lansdorp, Vancouver (CA); Kasmintan Schrader, Vancouver (CA); Steven Jones, Vancouver (CA); Vincent Hanlon, Vancouver (CA); Vahid Akbari, Vancouver (CA); Kieran O'Neill, Vancouver (CA)

(73) Assignee: Provincial Health Services Authority, Vancouver (CA)

( * ) Notice: Subject to any disclaimer, the term of this patent is extended or adjusted under 35 U.S.C. 154(b) by 0 days.

(21) Appl. No.: 18/518,079

(22) Filed: Nov. 22, 2023

(65) Prior Publication Data
US 2024/0102082 A1  Mar. 28, 2024

Related U.S. Application Data

(63) Continuation of application No. PCT/CA2023/050642, filed on May 10, 2023.
(Continued)

(51) Int. Cl.
*C12Q 1/6809* (2018.01)
*C12Q 1/6883* (2018.01)
(Continued)

(52) U.S. Cl.
CPC ......... *C12Q 1/6809* (2013.01); *C12Q 1/6883* (2013.01); *G16B 20/20* (2019.02);
(Continued)

(58) Field of Classification Search
CPC ............... C12Q 1/6809; C12Q 1/6883; C12Q 2600/154; C12Q 2600/156;
(Continued)

(56) References Cited

U.S. PATENT DOCUMENTS 9,797,005 B2   10/2017   Campan et al.
2012/0283108 A1   11/2012   Sampas
(Continued)

FOREIGN PATENT DOCUMENTS

AU   2001274866 B2   11/2006
AU   2004281299 B2   11/2010
(Continued)

OTHER PUBLICATIONS

Angers, A. et al. Whole Genome Sequencing and forensic genomics, EUR 30766 EN, Publications Office of the European Union, Luxembourg, 2021, ISBN 978-92-76-40265-7, doi:10.2760/864087, JRC125734. (Year: 2021).*
(Continued)

*Primary Examiner* — Diana B Johannsen
(74) *Attorney, Agent, or Firm* — Viridant IP

(57) ABSTRACT

A method of assigning parent-of-origin to a haplotype, a sub-haplotype or an allele associated with a haplotype. Chromosome-length haplotypes of a genome are generated and a differential methylation status of at least one imprinted differentially methylated region (iDMR) associated with each one of the autosomal chromosomes is determined. The differential methylation status of the at least one iDMR is used to assign parent-of-origin for each one of the chromosome-length haplotypes.

7 Claims, 7 Drawing Sheets

Related U.S. Application Data

(60) Provisional application No. 63/340,712, filed on May 11, 2022.

(51) Int. Cl.
    *G16B 20/20*     (2019.01)
    *G16B 30/10*     (2019.01)

(52) U.S. Cl.
    CPC ....... *G16B 30/10* (2019.02); *C12Q 2600/154* (2013.01); *C12Q 2600/156* (2013.01)

(58) Field of Classification Search
    CPC .. C12Q 2600/172; G16B 30/10; G16B 20/00; G16B 20/20
    See application file for complete search history.

(56) References Cited

U.S. PATENT DOCUMENTS

| | | |
|---|---|---|
| 2014/0045706 A1 | 2/2014 | Fan et al. |
| 2015/0205913 A1 | 7/2015 | He et al. |
| 2022/0010380 A1 | 1/2022 | Hoyo et al. |
| 2022/0177961 A1 | 6/2022 | Ren et al. |

FOREIGN PATENT DOCUMENTS

| | | | |
|---|---|---|---|
| CA | 2692844 A1 | 12/2008 | |
| WO | 2004081721 A2 | 9/2004 | |

OTHER PUBLICATIONS

Mahmoud, M. et al. Genome Biology 20:246. (Year: 2019).*
Akbari, V. et al. bioRxiv preprint, doi.org/10.1101/2021.07.17.452734, 29 pages. Jul. 18, 2021. (Year: 2021).*
Fishbein, L. et al. Cancer Genetics 205:1-11. (Year: 2012).*
Akbari V, Hanlon VCT, O'Neill K, Lefebvre L, Schrader KA, Lansdorp PM, Jones SJM. Parent-of-origin detection and chromosome-scale haplotyping using long-read DNA methylation sequencing and Strand-seq. Cell Genom. Dec. 21, 2022;3(1):100233. doi: 10.1016/j.xgen.2022.100233.
Akbari, V., Garant, JM., O'Neill, K. et al. Megabase-scale methylation phasing using nanopore long reads and NanoMethPhase. Genome Biol 22, 68 (2021). https://doi.org/10.1186/s13059-021-02283-5.
Gigante S, Gouil Q, Lucattini A, Keniry A, Beck T, Tinning M, Gordon L, Woodruff C, Speed TP, Blewitt ME, Ritchie ME. Using long-read sequencing to detect imprinted DNA methylation. Nucleic Acids Res. May 7, 2019;47(8):e46. doi: 10.1093/nar/gkz107.
Akbari, V. et al. (2022) Genome-wide detection of imprinted differentially methylated regions using nanopore sequencing eLife 11:e77898.
Porubsky, D., Ebert, P., Audano, P.A. et al. Fully phased human genome assembly without parental data using single-cell strand sequencing and long reads. Nat Biotechnol 39, 302-308 (2021). https://doi.org/10.1038/s41587-020-0719-5.
Rand, A., Jain, M., Eizenga, J. et al. Mapping DNA methylation with high-throughput nanopore sequencing. Nat Methods 14(4), 411-413 (2017). https://doi.org/10.1038/nmeth.4189.
Li Y, Li J. Technical advances contribute to the study of genomic imprinting. PLoS Genet. Jun. 20, 2019;15(6): e1008151. doi: 10.1371/journal.pgen.1008151.
Porubsky, D., Garg, S., Sanders, A.D. et al. Dense and accurate whole-chromosome haplotyping of individual genomes. Nat Commun 8, 1293 (2017). https://doi.org/10.1038/s41467-017-01389-4.
Jain, M. et al. Nanopore sequencing and assembly of a human genome with ultra-long reads. Nat. Biotechnol., vol. 36 (4), 2018, pp. 338-345.
Ebert, P. et al. Haplotype-resolved diverse human genomes and integrated analysis of structural variation. Science 372, doi:10.1126/science.abf7117 (2021).
Porubsky, D. et al. Direct chromosome-length haplotyping by single-cell sequencing. Genome Res 26(11), 1565-1574, doi:10.1101/gr.209841.116 (2016).
Zheng et al., Nat Biotechnol. 2016, 34(3):303-311.
Sticca et al., Current Developments in Detection of Identity-by-Descent Methods and Applications, Front. Genet., vol. 12, 2021. Article 722602 (6 pages).
Lee, et al. Simultaneous profiling of chromatin accessibility and methylation on human cell lines with nanopore sequencing. Nat Methods 17, 1191-1199, 2020.
Falconer E, Hills M, Naumann U, Poon SS, Chavez EA, Sanders AD, et al. DNA template strand sequencing of single-cells maps genomic rearrangements at high resolution. Nat Methods. 2012;9(11):1107-12.
Hanlon VCT, Chan DD, Hamadeh Z, Wang Y, Mattsson CA, Spierings DCJ, et al. Construction of Strand-seq libraries in open nanoliter arrays. Cell Rep Methods. 2022;2(1):100150.
Liao WW, Asri M, Ebler J, Doerr D, Haukness M, Hickey G, et al. A draft human pangenome reference. Nature. 2023;617(7960):312-24.
Logsdon GA, Rozanski AN, Ryabov F, Potapova T, Shepelev VA, Catacchio CR, et al. The variation and evolution of complete human centromeres. Nature. 2024;629(8010):136-45.
Porubsky D, Hops W, Ashraf H, Hsieh P, Rodriguez-Martin B, Yilmaz F, et al. Recurrent inversion polymorphisms in humans associate with genetic instability and genomic disorders. Cell. 2022;185(11):1986-2005 e26.
Ebert P, Audano PA, Zhu Q, Rodriguez-Martin B, Porubsky D, Bonder MJ, et al. Haplotype-resolved diverse human genomes and integrated analysis of structural variation. Science. 2021;372(6537).
Akbari V, Hanlon VCT, O Neill K, Lefebvre L, Schrader KA, Lansdorp PM, et al. Parent-of-origin detection and chromosome-scale haplotyping using long-read DNA methylation sequencing and Strand-seq. Cell Genomics. 2022:100233.
Porubsky D, Sanders AD, van Wietmarschen N, Falconer E, Hills M, Spierings DC, et al. Direct chromosome-length haplotyping by single-cell sequencing. Genome research. 2016;26(11):1565-74.
Porubsky D, Ebert P, Audano PA, Vollger MR, Harvey WT, Marijon P, et al. Fully phased human genome assembly without parental data using single-cell strand sequencing and long reads. Nat Biotechnol. 2021;39(3):302-8.
Porubsky D, Garg S, Sanders AD, Korbel JO, Guryev V, Lansdorp PM, et al. Dense and accurate whole-chromosome haplotyping of individual genomes. Nat Commun. 2017;8(1):1293.
Chaisson MJP, Sanders AD, Zhao X, Malhotra A, Porubsky D, Rausch T, et al. Multi-platform discovery of haplotype-resolved structural variation in human genomes. Nat Commun. 2019;10(1):1784.
Hofmeister, R.J., Rubinacci, S., Ribeiro, D.M et al. Parent-of-Origin inference for biobanks. Nat Commun 13, 6668 (2022).
Elliott P, Peakman TC; UK Biobank. The UK Biobank sample handling and storage protocol for the collection, processing and archiving of human blood and urine. Int J Epidemiol. Apr. 2008;37(2):234-44. doi: 10.1093/ije/dym276.
Rautiainen, M., Nurk, S., Walenz, B.P., Logsdon, G.A., Porubsky, D., Rhie, A., Eichler, E.E., Phillippy, A.M., and Koren, S. (2023). Telomere-to-telomere assembly of diploid chromosomes with Verkko. Nat. Biotechnol. https://doi.org/10. 1038/s41587023 01662 01666.
Richards S, Aziz N, Bale S, Bick D, Das S, Gastier-Foster J, Grody WW, Hegde M, Lyon E, Spector E, Voelkerding K, Rehm Hl; Acmg Laboratory Quality Assurance Committee. Standards and guidelines for the interpretation of sequence variants: a joint consensus recommendation of the American College of Medical Genetics and Genomics and the Association for Molecular Pathology. Genet Med. May 2015;17(5):405-24.
Baysal BE, Ferrell RE, Willett-Brozick JE, Lawrence EC, Myssiorek D, Bosch A, van der May A, Taschner PEM, Rubinstein WS, Myers EN, Richard III CW, Cornelisse CJ, Devilee P, Devlin B (2000) Mutations in SDHD, a mitochondrial complex II gene, in hereditary paraganglioma. Science 287:848-851.
Reik W, Maher ER. Imprinting in clusters: lessons from Beckwith-Wiedemann syndrome. Trends Genet. Aug. 1997;13(8):330-4.

(56) References Cited

OTHER PUBLICATIONS

Zhou H, Brockington M, Jungbluth H, Monk D, Stanier P, Sewry CA, Moore GE, Muntoni F. Epigenetic allele silencing unveils recessive RYR1 mutations in core myopathies. Am J Hum Genet. Nov. 2006;79(5):859-68.

Green RC, Berg JS, Grody WW, Kalia SS, Korf BR, Martin CL, McGuire AL, Nussbaum RL, O'Daniel JM, Ormond KE, Rehm HL, Watson MS, Williams MS, Biesecker LG; American College of Medical Genetics and Genomics. ACMG recommendations for reporting of incidental findings in clinical exome and genome sequencing. Genet Med. Jul. 2013;15(7):565-74.

Miller DT, Lee K, Abul-Husn NS, Amendola LM, Brothers K, Chung WK, Gollob MH, Gordon AS, Harrison SM, Hershberger RE, Klein TE, Richards CS, Stewart DR, Martin CL; ACMG Secondary Findings Working Group. Electronic address: documents@acmg.net. ACMG SF v3.2 list for reporting of secondary findings in clinical exome and genome sequencing: A policy statement of the American College of Medical Genetics and Genomics (ACMG). Genet Med. Aug. 2023;25(8):100866.

Zink F, Magnusdottir DN, Magnusson OT, Walker NJ, Morris TJ, Sigurdsson A, Halldorsson GH, Gudjonsson SA, Melsted P, Ingimundardottir H, Kristmundsdottir S, Alexandersson KF, Helgadottir A, Gudmundsson J, Rafnar T, Jonsdottir I, Holm H, Eyjolfsson GI, Sigurdardottir O, Olafsson I, Masson G, Gudbjartsson DF, Thorsteinsdottir U, Halldorsson BV, Stacey SN, Stefansson K. Insights into imprinting from parent-of-origin phased methylomes and transcriptomes. Nat Genet. Nov. 2018;50(11):1542-1552.

Alekseeva EA, Babenko OV, Kozlova VM, Ushakova TL, Kazubskaya TP, Nemtsova MV, Chesnokova GG, Mikhaylenko DS, Bure IV, Kalinkin AI, Kuznetsova EB, Tanas AS, Kutsev SI, Zaletaev DV, Strelnikov VV. Parental Origin of the RB1 Gene Mutations in Families with Low Penetrance Hereditary Retinoblastoma. Cancers (Basel). Oct. 10, 2021;13(20):5068.

Nakamichi K, Stacey A, Mustafi D. Targeted long-read sequencing allows for rapid identification of pathogenic disease-causing variants in retinoblastoma. Ophthalmic Genet. Dec. 2022;43(6):762-770.

A comprehensive workflow for target adaptive sampling long-read sequencing applied to hereditary cancer patient genomes. Wataru Nakamura, Makoto Hirata, Satoyo Oda, Kenichi Chiba, Ai Okada, Ral Nicols Mateos, Masahiro Sugawa, Naoko Iida, Mineko Ushiama, Noriko Tanabe, Hiromi Sakamoto, Yosuke Kawai, Katsushi Tokunaga, NCBN Controls WGS Consortium, Shinichi Tsujimoto, Norio Shiba, Shuichi Ito, Teruhiko Yoshida, Yuichi Shiraishi. medRxiv 2023.05.30.23289318.

* cited by examiner

METHOD FOR PARENT-OF-ORIGIN DISEASE ALLELE DETECTION FOR THE DIAGNOSIS AND MANAGEMENT OF GENETIC DISEASES

REFERENCE TO RELATED APPLICATIONS

This application is a continuation of Patent Cooperation Treaty patent application No. PCT/CA2023/050642 filed 10-5-2023, which claims priority to, and for purposes of the United States of America the benefit of, U.S. provisional patent application No. 63/340,712 filed 11-5-2022. Both of the foregoing applications are incorporated by reference herein for all purposes in their entireties.

TECHNICAL FIELD

Some embodiments relate to methods or apparatus for determining a parent-of-origin of a haplotype, of a sub-haplotype, or of an allele in a mammalian subject. Some embodiments relate to methods or apparatus for determining a parent-of-origin of a haplotype, a sub-haplotype or an allele in a mammalian subject without use of parental sequence information.

BACKGROUND

Although phasing is conventionally defined as the task of distinguishing alleles from maternal and paternal homologs, in practice most current phasing methods neglect parental information entirely. Instead, chromosomes are either described as a series of subchromosomal phase blocks, each of which consists of alleles grouped into two haplotypes (for diploids) or chromosome-length phase blocks that are not assigned a parent of origin (PofO). In this sense, true phase information is largely out of reach for current genomic methods that do not incorporate sequence data from at least one parent next to the child[1-3].

A striking exception to this paradigm is the parental information provided by consistent differences in DNA methylation between maternally- and paternally-inherited alleles at imprinted differentially methylated regions (iDMRs). Such iDMRs reliably suppress the expression of either maternal or paternal alleles and, crucially, can be detected for example using the unique ion current signature of 5-methyl-cytosine by nanopore sequencing (Oxford Nanopore Technologies)[4-7]. Long nanopore sequence reads can be used to call both sequence variation and DNA methylation to detect genome-wide allele-specific methylation[6,7]. Despite the fact that phasing using nanopore reads can achieve megabase-scale phase blocks, full chromosome haplotypes cannot be obtained and each chromosome is represented in several phase blocks with likely switches between the paternal and maternal origin of the blocks along the chromosome[6].

Conversely, some phasing techniques lack parental information but produce phase blocks that span centromeres, repetitive regions, and runs of homozygosity[8,9]. For example, single-cell Strand-seq is a method that enables sequencing of parental DNA template strands in single daughter cells cultured for one DNA replication round in the presence of BrdU[10]. Reads from Watson template strands map to the reference genome in the minus orientation and reads from Crick template strands map in the plus orientation, meaning that alleles covered by reads with different orientations that occur at a frequency of 50% for a given chromosome belong to different homologs. By sequencing multiple cells, this approach enables the construction of global, chromosome-length haplotypes[8]. Because Strand-seq phase blocks are generally sparse (i.e., they do not phase all single nucleotide variants; SNVs), Strand-seq often serves as a scaffold upon which reads or subchromosomal phase blocks from other sequencing techniques are combined, effectively phasing them relative to each other along the entire length of a given chromosome[1,12].

Determining PofO for germline variants can aid in clinical genetics. Genetic testing can inform a patient's inherited risk for disease. However, predicting which side of the family an autosomal variant comes from is a key limitation of current technology. Inability to determine a variant's parent-of-origin (PofO) (i.e., if it is maternally or paternally inherited) can lead to uncertain patient management and ineffective cascade genetic testing (CGT).

The impact of missing PofO information on in clinical genetics practice can be illustrated within a framework considering the Patient, Family, and Health Care System. In consideration of the impact of missing PofO information on the patient one may consider genes with PofO effects. There are genes that require parental segregation of pathogenic/likely pathogenic variants (PV) to interpret disease risks. This is the most direct use for determining PofO. Germline PV in SDHD demonstrate PofO effects and predispose to high lifetime risks for paragangliomas and phaechromocytomas when inherited through the father[68,69]. Accurate prediction of maternal PV inheritance allows the patient to avoid lifelong annual disease screening that requires high-resolution magnetic resonance imaging, biochemical tests and specialist assessments. These carry direct and indirect costs to both the patient and healthcare system. Without knowledge of PofO, patients may be advised to continue screening or are given unclear direction leading to non-adherence to screening. Unnecessary and costly procedures or missed tumour diagnoses can result. Segregation of the variant by parental CGT may not be possible when parents are deceased, unavailable or decline genetic testing. In this regard, PofO assignment enables immediate improved cancer risk assessment for the patient.

In consideration of the impact of missing PofO information on screening recommendations, one may consider management recommendations that are dependent on phenotypic segregation. Pancreatic ductal adenocarcinoma (PDAC) screening is 10 recommended to BRCA1, BRCA2, MLH1, MSH2, ATM, PALB2 PV carriers with PDAC in close relatives from the same side of the family as the PV. However, segregation is typically unknown. When parents are deceased, tissue testing can segregate the PV, however in the case of PDAC, there is usually limited or no archival tissue. Pancreatic cancer screening is invasive (e.g., annual alternating upper endoscopy and magnetic 15 resonance imaging (MRI)), stressful, burdensome to patients, and costly to the system. PofO assignment that predicts non-segregation could potentially release PV carriers from PDAC screening or if found to predict segregation with the PV, could make it available to them.

In consideration of the impact of missing PofO information on variant curation, one may consider variant curation guidelines that take into account phenotypic segregation within the family. Upgrading or downgrading variants from "variant of uncertain significance" (VUS) can impact cancer screening/surveillance and risk-reduction interventions (e.g., surgical or medical). VUS are typically encountered in 40% of index cases tested by multigene panel or genomic approaches. Currently the ACMG/AMP guidelines use phenotypic information and variant segregation to guide variant classifications[15]. Determining the phase or whether variants are in cis or trans with other PV can also be used to classify variants[15]. Suspicious variants of uncertain significance that are unable to achieve pathogenic or benign variant classifications may benefit from alternative evidence such as haplotyping and prediction of segregation to support variant classification.

In consideration of the impact of missing PofO information on the Family, one may consider the risk of recurrence for pathogenic variants to occur in another pregnancy. In the setting of de novo variants, PofO assignment can inform recurrence risk for a pathogenic variant to occur in another pregnancy depending on the PofO assignment and whether the predicted parent of origin of the variant in question is a parent of the current pregnancy/embryo/fetus or child in question. For example, if a de novo pathogenic variant was predicted to have come from the father there may be a risk for gonadal mosaicism for that pathogenic variant in a subsequent pregnancy. However, if the subsequent pregnancy was with the same mother but a different father, there would be no significant risk for that pathogenic variant and may be no need for amniocentesis or other investigations to assess for that pathogenic variant. In addition, identification of a parent that may be potentially mosaic for a pathogenic variant, may also indicate they are at increased risk for cancer; these individuals may benefit from increased cancer screening.

In consideration of the impact of missing PofO information on the clarification of PV risk estimates, one may consider the a priori risks assigned to parents to carry an autosomal dominant PV prior to segregation testing that are typically around 50% each. Accurate prediction of PV PofO alters a priori risk estimates of family members to carry the PV. As one parent moves from 50% to ~100% chance to carry the PV, the other parent and their extended relatives move from 50% to ~0%, usually putting them back to population risk for cancer. Second-degree relatives (e.g. an aunt) from the side of the family segregating the PV move from 25% to ~50% chance to carry the PV. In certain jurisdictions, individuals at 50% chance of carrying a PV in a high penetrant breast cancer susceptibility gene (e.g. BRCA1) can access annual breast MRI screening until their genetic status is clarified. Considering the lack of PV segregation in most second-degree relatives, the potential to change medical management of second-degree relatives with use of PofO prediction in the proband is highly significant.

In consideration of the impact of missing PofO information on Cascade Genetic Testing (CGT), one may consider the a priori risks assigned to parents to carry an autosomal dominant PV prior to segregation testing that are typically around 50% each and currently poor cascade genetic testing rates. Using PofO prediction to target CGT throughout a family could yield the most significant impact to the health care system. For example, estimating less than 10% of the predicted 300,000 Canadians with hereditary cancer (HC) susceptibility have been identified in the last 25 years, there remains high unmet public service need to improve CGT rates. Hereditary breast and ovarian cancer (HBOC), due to germline PV in BRCA1 or BRCA2, is associated with substantially elevated life-time risks for breast, ovarian, prostate and pancreatic cancer. Lynch syndrome (LS), due to germline PV in MLH1, MSH2, MSH6, or PMS2, predisposes to colon and endometrial cancer. These are two of the most common hereditary cancer syndromes. The Centers for Disease Control and Prevention (CDC), Office of Genomics and Precision Public Health (OGPPH) recognise HBOC and LS as having Tier 1 evidence for "significant potential for positive impact on public health based on available evidence-based guidelines and recommendations" where identification of these hereditary cancer syndromes have both treatment and targeted cancer risk reduction utility in patients and family members. Genetic testing for these and other hereditary cancer syndromes has been available since the mid-nineties. Despite the potential to prevent or catch cancers early, uptake of CGT remains poor with no relative presenting for CGT in half of the families identified[20, 71]. Lower rates are also consistently observed within ethnic minority populations[20], which may be driven by limited intrafamily communication, unavailable relatives, or fractured family structures. Challenges to CGT include when cancer susceptibility PV are identified outside of the context of a known family history of cancer, as seen in universal screening for Lynch syndrome[19,71] germline multigene panel testing for hereditary cancer[72] and tumour testing for targeted treatment indications[73]. This unmet potential necessitates the development of new strategies and technologies to increase identification of at-risk family members. Groups are developing guidelines to enable patient-sanctioned direct contact of relatives (PSDCoR), shown to be effective at increasing rates of CGT[74]. PSDCoR will dramatically increase the number of patients undergoing CGT across all ethnicities necessitating the commitment of additional resources to actively seek out at-risk family members. Offering CGT to parents is the first step in identification of at-risk extended relatives, however, parental samples are frequently unavailable. Adoption of accurate PofO prediction can significantly reduce CGT expenses, decrease time to diagnosis and improve risk assessments by determining upfront, which side of the family is at risk. While the focus on cost is often on the actual molecular test, until segregation is confirmed, significant resources can be expended on pre-test genetic counselling for multiple family members on both sides of the family. Direct and indirect financial and emotional burdens are also associated with CGT of a patient's family members. Accurate PofO prediction will halve the number of family members requiring CGT, double the mutation detection rate and achieve these outcomes at lower costs per family. With an average family size of n=20[32], accurate PofO prediction will be critical to achieve the scale of testing generated from PSDCoR, in an efficient and cost-effective manner. Low-cost genetic testing of all relatives may be regarded as a competitor to parent-of-origin-aware genomic analysis (POAga), however, if segregation is not possible, relying on testing of both sides of the family may cause undue burden to the side not actually at-risk, increase clinical infrastructure costs, occupy limited genetic counseling resources and possibly delay CGT in the at-risk side by diluting the risk perception across both sides of the family and decreasing the sense of urgency. Accurate PofO prediction may save money, improve risk assessments, and time to diagnosis.

In consideration of the impact of missing PofO information on the Health Care System, better identification of PV carriers and cancer prevention or early-detection at a more treatable stage, has the potential to alleviate significant economic pressure on an overburdened healthcare system. Population genetic testing (PGT) may be seen as superseding CGT, however the need for CGT depends on how quickly and evenly PGT can be implemented. Considering the poor uptake of CGT in HC families at increased risk for cancer, PGT in individuals at average risk may prove more challenging. It is unclear how rapidly adoption and saturation of PGT will occur. Of note, the two approaches are not mutually exclusive. Even with PGT, the clinic would still ensure that relatives within HC families have been tested. Family members may have opted out of PGT due to low perceived risk, or may have had limited access to PGT (e.g. over 20% of Canadians are recent immigrants). Furthermore, ethnic minorities have the poorest CGT rates[20], therefore a PSDCoR approach in HC and other families with heritable disease risks may be necessary instead of relying on those at-risk to present or uptake PGT. Accurate prediction of PofO through POAga is of significant value to health care systems where the timeline for adoption of PGT is years away. Prior to the adoption of PGT, POAga-facilitated PSDCoR of individuals with PV identified from peridiagnostic cancer genetic testing could make real gains in improving CGT rates and identifying all HC PV in the population within 10 years if 70% of first degree, second degree and third degree relatives were tested[32]. Finally, once PGT is established, POAga will still be critical to ensure those at highest risk have been identified and in redefining risks for family members who have declined both PGT and CGT, in order to best inform their medical management. Use of POAga will be necessary to realize the full potential of precision health care, now and in the future.

In summary, accurate assignment of variant PofO can aid in clinical genetics in a number of ways including: curating variants, determining recurrence risk in a future pregnancy for an apparent de novo variant identified in a conceptus, fetus or child, efficiently screening relatives for genetic disease, predicting segregation of cancer or other disease susceptibility risk to direct management recommendations, and evaluating disease risk when a pathogenic variant has PofO effects, that is, when a patient's risk of disease depends on from which parent it is inherited (e.g. hereditary paraganglioma-pheochromocytoma syndrome due to pathogenic variants in SDHD, SDHAF2 and MAX)[13-17]. Cascade genetic testing is used for pathogenic variants associated with diseases such as hereditary cancers or other actionable Mendelian disease risks with the goal of preventing or catching cancers early, or intervening in disease or disease risk, in family members[18]. In the absence of PofO information due to parents being unavailable, deceased, or declining genetic testing, cascade genetic testing must be offered to both sides of the family until segregation is confirmed. This may be costly and burdensome to patients and families, exacerbating already low rates of uptake of cascade genetic testing[19,20]. Eliminating the need to test one side of the family is a clear benefit and a major clinical utility of defining PofO for pathogenic variants, and more broadly, establishing chromosome-length haplotypes with accurate parental segregation of genomic variation has widespread applications.

There is a general desire for improved methods of determining parent-of-origin for alleles associated with various conditions or diseases, and in particular methods that do not require sequence data from family members.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect provides a method of assigning parent-of-origin to a haplotype, sub-haplotype, or allele associated with the haplotype. Chromosome-length haplotypes of a genome are generated. A differential methylation status of at least one imprinted differentially methylated region (iDMR) associated with each autosomal chromosome of the subject is determined. The determined differential methylation status of the at least one iDMR is correlated to each one of the chromosome-length haplotypes to assign a parent-of-origin for each one of the chromosome-length haplotypes, including the sub-haplotypes and alleles associated with that haplotype. In some aspects, the step of generating chromosome-length haplotypes is conducted by using at least one sequencing method. In some aspects, rather than assembling chromosome-length haplotypes, partial haplotypes are generated.

In one aspect, the chromosome-length haplotypes are determined by conducting a first sequencing method that enables determination of long-range phase information and a second sequencing method that enables accurate determination of at least short reads of sequence and assignment of those short reads of sequence to a haplotype. The results from the first and second sequencing methods are used to generate chromosome-length haplotypes. A methylation status of at least one iDMR associated with each autosomal chromosome of the subject is determined, optionally using the second sequencing method, and the determined methylation status of the at least one iDMR is used to assign a parent-of-origin for each one of the chromosome-length haplotypes. In some aspects, the results of the first and second sequencing methods are used iteratively to generate the chromosome-length haplotypes.

In some aspects, the method is used to assign parent-of-origin to a haplotype, sub-haplotype or an allele associated with the haplotype using only a sample obtained from the subject, i.e. without reference to parental or familial sequence data, by evaluating a methylation status of iDMRs associated with each one of a pair of haplotypes of the subject.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Figures 1, 2:
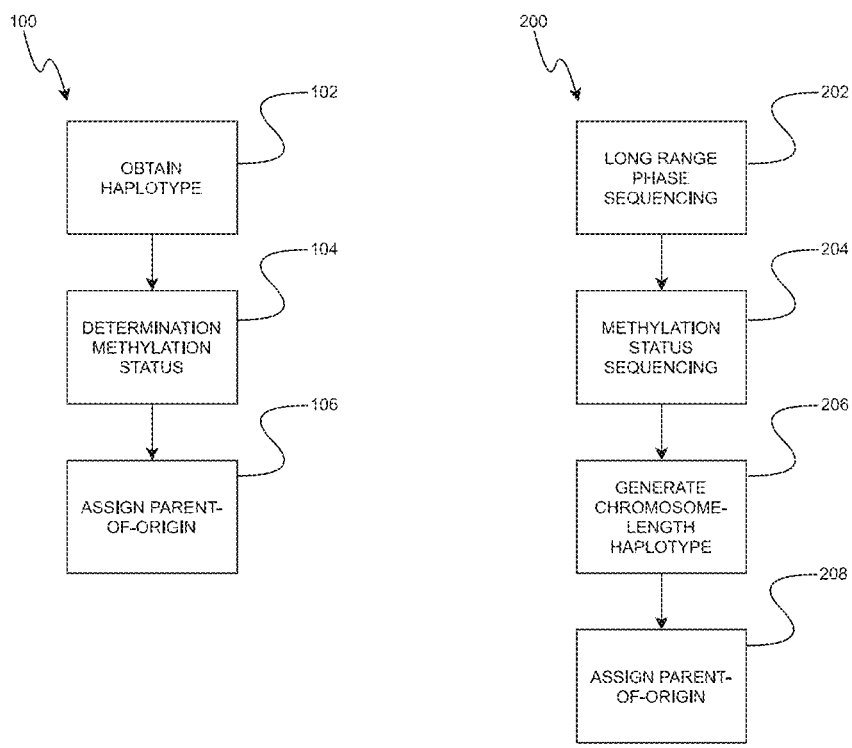
FIG. 1 shows an example embodiment of a method for determining parent-of-origin of a haplotype, sub-haplotype or allele associated with the haplotype.
FIG. 2 shows a second example embodiment of a method for determining parent-of-origin of a haplotype, sub-haplotype or allele associated with the haplotype.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Hundreds of loci in human genomes have alleles that are methylated differentially according to their parent of origin. The DNA methylation at these imprinted loci, referred to as imprinted differentially methylated regions or iDMRs, generally show little variation across tissues, individuals, and populations. The inventors have demonstrated that such loci can be used to distinguish the maternal and paternal homologs for all autosomes, without the need for the parental DNA. The inventors have integrated a determination of the methylation status of iDMRs using a methylation-detecting sequencing technique (nanopore sequencing in the exemplified embodiment) with the long-range phase information obtained using another sequencing technique (Strand-seq in the exemplified embodiment) to determine the parent of origin of chromosome-length haplotypes for both DNA sequence and DNA methylation. The inventors have demonstrated that the overlap between SNVs in iDMRs and SNVs defined by a sequencing strategy that enables determination of long-range phase information, e.g. Strand-seq, enables, for the first time, complete parent-of-origin aware haplotyping or phasing without analysis of parental genomes. The inventors verified the determination of parent-of-origin in five trios from a variety of global populations. The inventors' method correctly infers the parent of origin for all autosomes with a low mismatch error rate. Because the method can determine whether an inherited disease allele may have originated from the mother or the father, the method can be used in the diagnosis, treatment and management of genetic diseases. Because the method can also determine whether any autosomal variant may have originated from the mother or the father, the method can also be used in the discovery, investigation, and exploration of genetic ancestry, inherited traits, pharmacogenomic variants and forensic studies.

Some embodiments provide methods and apparatus to assign the parent-of-origin of autosomal alleles using parental imprints and chromosome-length haplotypes. In one aspect the invention provides methods and apparatus for the assignment of greater than 99% of the autosomal alleles to a parent of origin.

Some embodiments provide methods and apparatus related to distinguishing alleles from maternal and paternal homologs to resolve the haplotypes of parental chromosomes in diploid genomes. In one aspect the invention provides methods and apparatus for resolving the haplotypes of human genomes. In alternative aspects this invention provides methods and apparatus for resolving the haplotypes of other mammalian and diploid genomes.

The invention provides a method to determine whether an inherited disease allele may have originated from the mother or the father of a subject for the diagnosis and management of genetic disease. Knowledge of parental segregation has implications regarding variant curation, understanding of disease penetrance, management implications in the patient and parents, and facilitating focused cascade genetic testing. Such diseases include but are not limited to inherited syndromes such as hereditary cancer syndromes which display parent-of-origin effects including hereditary paraganglioma-pheochromocytoma syndrome associated with SDHD, SDHAF2 and MAX and other inherited cancer syndromes such as Hereditary Breast and Ovarian Cancer, Lynch syndrome, and others. Diseases also include but are not limited to actionable cancer and non-cancer related diseases and include but are not limited to those identified by the American College of Medical Genetics and Genomics (ACMG) Recommendations for Reporting of Incidental Findings in Clinical Exome and Genome Sequencing. Some embodiments of the invention can be applied to any mendelian disease or trait. These can be found in the Online Mendelian Inheritance in Man (OMIM®) which is a continuously updated catalog of human genes and genetic disorders and traits. Some embodiments of the invention can be applied to pharmacogenomic variants and markers of ancestry. Some embodiments of the invention can reveal somatic mutational signatures passed from either parent to child that may impact a child's risk for cancer or disease and may infer an ongoing mutational process in the parent that may be relevant to the parent's own cancer risk or disease status.

In one aspect, the invention provides a method of identifying the parental origin of an allele with limited or no access to parental and/or family DNA samples. In another aspect, the invention provides a method of identifying the parental origin of an allele that may be mosaic in the parent, which may inform recurrence risk or risk of disease to the parent who may have otherwise tested negative for the allele or pathogenic or likely pathogenic variant.

In one aspect, the invention provides a method for the identification, validation and screening of complex genetic traits for mammalian and diploid genomes. In one aspect, the invention provides a method for livestock genotyping for animal breeding.

In another aspect, the invention provides a method for delineating ancestral background from either parent.

In another aspect, the invention enables improved haplotyping for use in pharmacogenomic assessment, HLA haplotyping, cancer vaccines, forensics, and treatments using allele specific suppression. For example, parent-of-origin effects have been observed relating to the HLA locus.[58, 59] Similarly, HLA haplotype can be important to predicting the efficacy of, and hence contribute to the selection of, cancer vaccines and/or cancer therapeutics.[60]

In another aspect, the invention provides insight into the complete set of variants inherited from either parent that may infer mutational processes that occurred in either parent.

In another aspect, the invention facilitates novel variant and gene discovery through segregation of alleles/variants/haplotypes with parental or familial disease phenotypes.

In another aspect, with accurate resolution of all autosomal variation inherited from each parent, polygenic risks and genetic and epigenetic modifiers, the method can be used to inform comprehensive risk evaluation of Mendelian traits. In another aspect, with accurate resolution of all autosomal variation inherited from each parent, polygenic risks and genetic and epigenetic modifiers, the method can be used to inform comprehensive risk evaluation of complex traits.

Some embodiments of the invention provide methods and apparatus that utilizes imprinted differentially methylated regions (iDMRs) based on their parent of origin to integrate megabase-scale phase blocks from nanopore sequencing with the long-range phase information in DNA from a sequencing technique able to produce only sparse phase blocks (e.g. Strand-seq data) to provide maternal and paternal homologs for all autosomes. In one aspect of the invention, nanopore sequencing is performed using a nanopore PromethION instrument. A person skilled in the art may elect alternative sequencing technologies.

With reference to FIG. 1, a general method 100 for determining parent-of-origin of a haplotype, a sub-haplotype or an allele in a diploid genome is illustrated. At step 102, a haplotype is obtained in any suitable manner, for example by suitable long-range sequencing techniques able to resolve haplotypes (e.g. Strand-seq sequencing, Hi-C sequencing, 3C-Seq sequencing, 10× sequencing, continuous long-read (CLR) sequencing, high-fidelity (HiFi) sequencing, Pore-C sequencing, or other suitable technique now known or later developed, or a combination thereof), or by sequencing a haploid cell. In some embodiments, the long-range sequencing techniques used are able to resolve haplotypes along the entire length of chromosomes.

At step 104, information as to the methylation status of imprinted differentially methylated regions (iDMRs) is determined for each haplotype, e.g. for each autosomal chromosome. The methylation status of the iDMRs can be determined in any suitable manner, for example using nanopore sequencing, single-molecule real-time (SMRT) sequencing, bisulfite sequencing, or other technique that allows a determination of the methylation status of iDMRs, whether now known or later developed, or a combination thereof.

In some embodiments, two different sequencing methods are used at steps 102 and 104 to determine both long-range phase information for each haplotype and methylation status of iDMRs associated with each one of the haplotypes. In other embodiments, if future developments in sequencing technology yield a single sequencing technique capable of determining both long-range phase information and the methylation status of iDMRs on each haplotype, then steps 102 and 104 could be conducted using that single sequencing technique.

In some embodiments, one sequencing technique is used both to assist with obtaining a haplotype at step 102 and to determine the methylation status of iDMRs associated with each haplotype at step 104. For example, in one embodiment, nanopore sequencing is used both at step 102 to assist in obtaining two haplotypes for a diploid genome, and at step 104 to determine the methylation status of a plurality of iDMRs associated with each one of the haplotypes. However, since nanopore sequencing cannot provide long-range phase information, the nanopore sequencing is combined with another sequencing technique at step 102, for example Strand-seq, Hi-C, 3C-Seq, 10×, continuous long-read (CLR), high-fidelity (HiFi), Pore-C or other sequencing technique that allows a determination of long-range phase information, in order to obtain complete haplotypes.

At step 106, the parent-of-origin for each haplotype is assigned based on the methylation status of the iDMRs for each one of the haplotypes, e.g. for each one of the autosomal chromosomes.

In some embodiments at step 102, rather than conducting a long-range sequencing, haplotypes constructed from haploid cells (e.g. sperm or egg), hypodiploid cell populations, or single chromosomes[57] can be sequenced to generate accurate haplotypes that sequence data from step 104 can be phased to. In some embodiments where the haplotypes are constructed from haploid cells such as sperm or egg, somatic tissue cells (for example blood) of the parent from which such haploid cells are obtained can be sequenced at step 104 to infer parent-of-origin from such parent's autosomal alleles, since the haploid cells (e.g. sperm or egg) would have themselves been imprinted in the course of formation.

With reference to FIG. 2, a second embodiment of a general method 200 for determining parent-of-origin of a haplotype, sub-haplotype or an allele for a diploid genome is illustrated. At step 202, a first sequencing method is carried out on a sample from a subject that allows a determination of long-range phase information for each one of the haplotypes of the diploid genome. Any suitable sequencing technique whether now known or later developed that allows a determination of long-range phase information can be used at step 202, for example, Strand-seq, Hi-C, 3C-Seq, 10×, continuous long-read (CLR), high-fidelity (HiFi), Pore-C, or a combination thereof.

At step 204, information as to the methylation status of imprinted differentially methylated regions (iDMRs) is determined for each haplotype, e.g. for each autosomal chromosome. The methylation status of the iDMRs can be determined in any suitable manner, for example using nanopore sequencing, single-molecule real-time (SMRT) sequencing, bisulfite sequencing, or other technique that allows a determination of the methylation status of iDMRs whether now known or later developed, or a combination of such techniques.

In some embodiments, two different sequencing methods are used at steps 202 and 204 to determine both long-range phase information for each haplotype and methylation status of iDMRs associated with each one of the haplotypes. In other embodiments, if future developments in sequencing technology yield a single sequencing technique capable of determining both long-range phase information and the methylation status of iDMRs on each haplotype, then steps 202 and 204 could be conducted using that single sequencing technique.

At step 206, chromosome-length haplotypes are generated using the sequence information obtained at steps 202 and 204. In some embodiments, the sequence information obtained at steps 202 and 204 is used iteratively to phase heterozygous variants such as single nucleotide variants (SNVs) and/or indels to obtain the chromosome-length haplotypes.

At step 208, a parent-of-origin is assigned to each one of the chromosome-length haplotypes using the results of the methylation status of the iDMRs associated with each one of the chromosome-length haplotypes (e.g. autosomal chromosomes) determined at step 206.

Figure 3A:
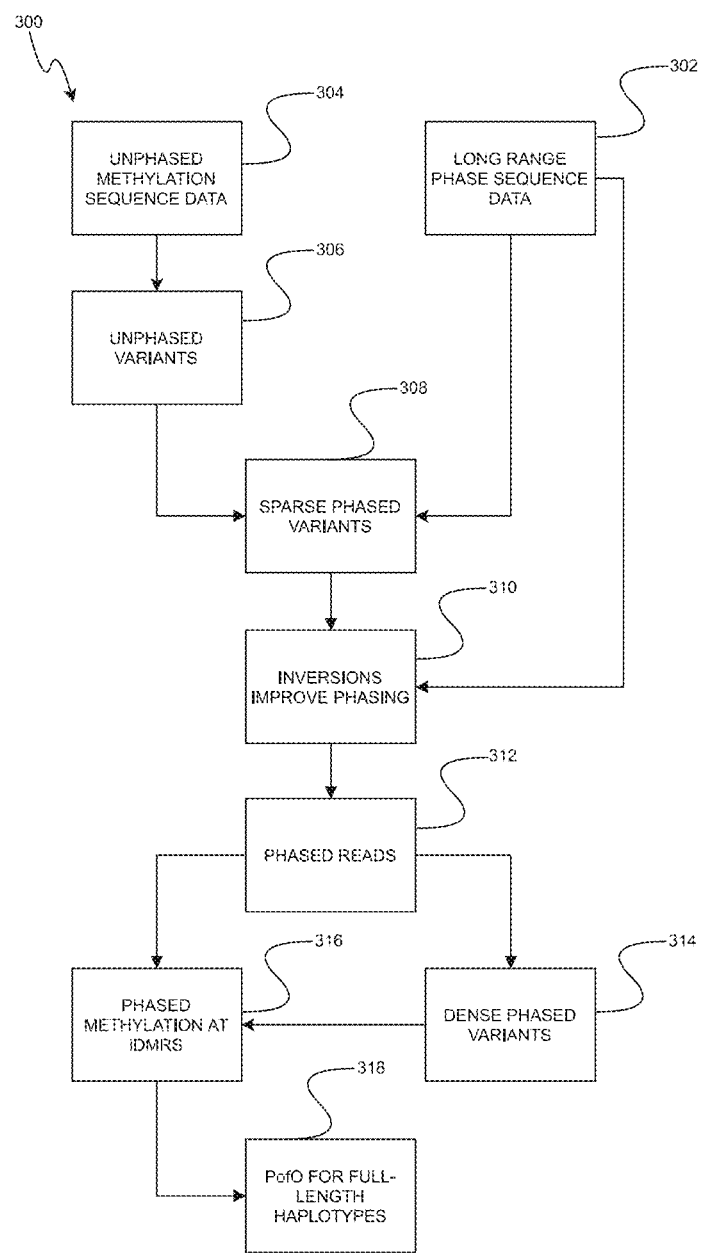
FIG. 3A shows a third example embodiment for determining parent-of-origin of a haplotype, sub-haplotype or allele associated with the haplotype.

With reference to FIG. 3A, a third example embodiment of one specific embodiment of a method 300 for determining parent-of-origin of a haplotype, sub-haplotype or an allele is illustrated. At step 302, a first sequencing method is carried out on a sample that allows a determination of long-range phase information for each one of the haplotypes of the diploid genome. For example, the first sequencing method may generate sparse chromosome-scale haplotypes. Any suitable sequencing technique whether now known or later developed that allows a determination of long-range phase information can be used at step 302, for example, Strand-seq, Hi-C, 3C-Seq, 10×, continuous long-read (CLR), high-fidelity (HiFi), Pore-C, or a combination thereof.

At step 304, a second sequencing method is carried out on the sample that allows determination of the methylation status of iDMRs associated with specific DNA sequences. The methylation status of the iDMRs can be determined in any suitable manner, for example using nanopore sequencing, single-molecule real-time (SMRT) sequencing, bisulfite sequencing, or other technique that allows a determination of the methylation status of iDMRs whether now known or later developed, or a combination of such techniques. The second sequencing method yields unphased variants (e.g. SNVs and/or indels) at 306.

At step 308 the long-range phase information for variants determined from the first sequencing method is used to phase variants obtained using the second sequencing method to one of the two haplotypes, i.e. HP1 or HP2. In some embodiments, the variants phased at step 308 are SNVs. In some embodiments, the variants phased at step 308 are indels and SNPs flanking the indel are used to assign the indel to a haplotype. In some embodiments, the variants phased at step 308 are both SNVs and indels.

In some embodiments, at step 310, the phased variants obtained at step 308 are used to rephase all variants (e.g. both SNVs and indels) identified by the first sequencing method to each haplotype, i.e. HP1 or HP2.

At step 312, the sequence reads obtained using the second sequencing method are phased a second time using all of the phased variants (e.g. both SNVs and indels) obtained in step 310 to yield dense phased variants at 314.

At step 316, per-read methylation information from each read obtained by the second sequencing method is integrated to its phase information from 314. Thus, the differential methylation information obtained at each iDMR is phased to each read in either one of the two haplotypes, i.e. HP1 or HP2, to calculate the methylation frequency at each iDMR site for each haplotype. The methylation frequency is then used to assign each haplotype to its parent-of-origin at 318 based on the methylation status of the known iDMRs.

Figure 3B:
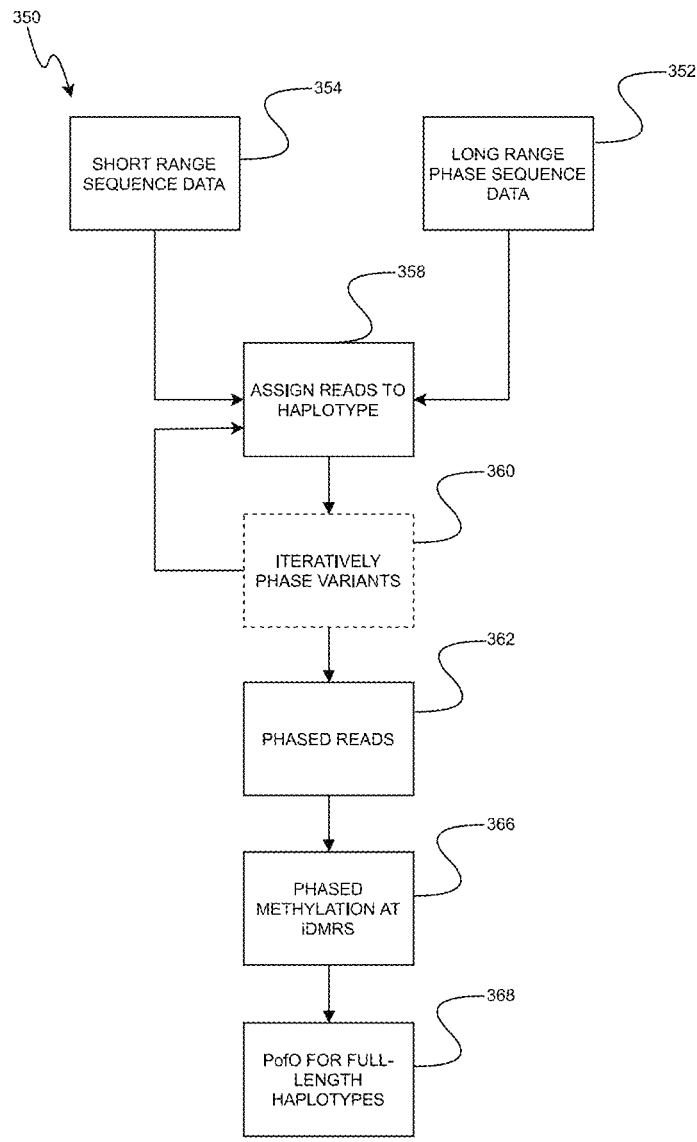
FIG. 3B shows a fourth example embodiment for determining parent-of-origin of a haplotype, sub-haplotype or allele associated with the haplotype.

With reference to FIG. 3B, a fourth example embodiment 350 of a method for determining parent of origin of a haplotype, sub-haplotype or an allele is illustrated. At step 352, a first sequencing method is carried out that enables determination of long-range phase information. At step 354, a second sequencing method is carried out that enables accurate determination of at least short reads of sequence and assignment of those short reads of sequence to a haplotype at 358. In some embodiments, the second sequencing method also provides information as to the methylation status of the short sequence reads. At step 360, variants (e.g. SNPs and/or indels) can optionally be iteratively phased to improve the phase information obtained at 362.

At step 366, the differential methylation status of at least one iDMR for each autosomal chromosome of the subject is determined, for example using information obtained from the second sequencing method. At 368, the parent-of origin for each one of the chromosome-length haplotypes is assigned based on the differential methylation status of the at least one iDMR for each autosomal chromosome of the subject.

In some embodiments, the method is used to assign parent-of-origin to a haplotype, sub-haplotype or an allele using only a sample obtained from a subject by evaluating a methylation status of iDMRs associated with each one of a pair of haplotypes of the subject.

In some embodiments, the method is used to trigger cascade genetic testing by selecting an undesirable sub-haplotype or allele or a sub-haplotype or allele of interest, determining a parent associated with the undesirable sub-haplotype or allele or the sub-haplotype or allele of interest based on the determination of parent-of-origin for the undesirable sub-haplotype or allele or the sub-haplotype or allele of interest, and conducting cascade genetic testing on family members of the parent associated with the undesirable sub-haplotype or allele or with the sub-haplotype or allele of interest. In some such embodiments, the undesirable allele is an allele of SDHD, SDHAF2, MAX, BRCA1, BRCA2, MLH1, MSH2, MSH6, PMS2, EPCAM, ATM, PALB2, TP53, APC, ACTA2, ACTC1, ACVRL1, AIP, ALK, ANKRD26, APOB, ARMC5, ATP7B, ATR, AXIN2, BAG3, BAP1, BARD1, BLM, BMPR1A, BRIP1, BTD, BUB1B, CACNA1S, CASQ2, CASR, CDC73, CDH1, CDK4, CDKN1B, CDKN1C, CDKN2A, CEBPA, CFTR, CHEK1, CHEK2, COL3A1, CPA1, CTC1, CTNNA1, CTRC, CYLD, DDB2, DDX41, DES, DICER1, DIS3L2, DKC1, DLST, DROSHA, DSC2, DSG2, DSP, EGFR, EGLN1, ENG, ERCC1, ERCC2, ERCC3, ERCC4, ERCC5, ETV6, EXT1, EXT2, EZH2, FAM175A, FAN1, FANCA, FANCB, FANCC, FANCD2, FANCE, FANCF, FANCG, FANCI, FANCL, FANCM, FBN1, FH, FLCN, FLNC, FOCAD, GAA, GALNT12, GATA2, GLA, GPC3, GREM1, HFE, HNF1A, HOXB13, HRAS, KCNH2, KCNQ1, KIF1B, KIT, LDLR, LMNA, LZTR1, MC1R, MEN1, MET, MITF, MLH3, MRE11, MRE11A, MSH3, MUTYH, MYBPC3, MYH11, MYH7, MYL2, MYL3, NBN, NF1, NF2, NHP2, NOP10, NTHL1, OTC, PAX5, PALLD, PCSK9, PDGFRA, PHOX2B, PIK3CA, PKP2, POLD1, POLE, POLH, POT1, PRKAG2, PRKAR1A, PRSS1, PTCH1, PTCH2, PTEN, RAB43, RABL3, RAD1, RAD50, RAD51C, RAD51D, RBI, RBM20, RECQL, RECQL4, RECQL5, REST, RET, RINT1, RPE65, RPS20, RUNX1, RYR1, RYR2, SAMD9, SAMD9L, SCN5A, SDHA, SDHB, SDHC, SLC45A2, SLX4, SMAD3, SMAD4, SMARCA4, SMARCB1, SMARCE1, SPINK1, SRP72, STK11, SUFU, TERC, TERT, TGFBR1, TGFBR2, TINF2, TMEM127, TMEM43, TNNC1, TNNI3, TNNT2, TP5313, TPM1, TRDN, TRIP13, TSC1, TSC2, TTN, TTR, TYR, VHL, WRAP53, WRN, WT1, XPA, XPC, or XRCC2, or any other gene currently known or later to be determined to be associated with a genetic disorder. A list of currently known actionable genetic disorders is available, for example, from the American College of Medical Genetics and Genomics. A list of currently known pathogenic variants of such genes is available, for example, from ClinVar, in for example ACTC1, ACVRL1, APC, APOB, ATP7B, BAG3, BMPR1A, BRCA1, BRCA2, BTD, CACNA1S, CASQ2, COL3A1, DES, DSC2, DSG2, DSP, ENG, FBN1, FLNC, GAA, GLA, HFE, HNF1A, KCNH2, KCNQ1, LDLR, LMNA, MAX, MEN1, MLH1, MSH2, MSH6, MUTYH, MYBPC3, MYH11, MYH7, MYL2, MYL3, NF2, OTC, PALB2, PCSK9, PKP2, PMS2, PRKAG2, PTEN, RBI, RBM20, RET, RPE65, RYR1, RYR2, SCN5A, SDHAF2, SDHB, SDHC, SDHD, SMAD3, SMAD4, STK11, TGFBR1, TGFBR2, TMEM127, TMEM43, TNNC1, TNNI3, TNNT2, TP53, TPM1, TRDN, TSC1, TSC2, TTN, TTR, VHL, and WT1.

In some embodiments, the undesirable allele is a founder mutation that is commonly associated with a genetic disorder, for example BRCA1 187delAG, BRCA1 5385insC (also described as BRCA1 5382insC), BRCA26174delT.

In some embodiments, if the allele is a mutant form of succinate dehydrogenase complex subunit D (SDHD) and the parent-of-origin is paternal, the method further comprises periodically evaluating the subject for paraganglioma or phaeochromocytoma and/or conducting cascade genetic testing. In some embodiments, if the allele is a mutant form of SDHD and the parent-of-origin is maternal, the method further comprises conducting cascade genetic testing.

In some embodiments, if the allele is a mutant form of succinate dehydrogenase complex assembly factor 2 (SDHAF2) and the parent-of-origin is paternal, the method further comprises periodically evaluating the subject for paraganglioma and/or conducting cascade genetic testing.

In some embodiments, if the allele is a mutant form of MYC-associated factor X gene (MAX) and the parent of-origin is paternal, the method further comprises periodically evaluating the subject for pheochromocytoma and/or conducting cascade genetic testing.

In some embodiments, if the allele is a mutant form of ATM, BRCA1, BRCA2, MLH1, MSH2, MSH6, EPCAM, PMS2, PALB2, TP53, CHEK2, BRIP1, RAD51C, RAD51D, or MUTYH and the parent-of-origin is determined to be a parent with a family history of pancreatic cancer, the method further comprises initiating pancreatic cancer screening in the subject beginning at age 50 years or 10 years younger than the earliest pancreatic cancer diagnosis in the family, whichever is earlier.

In some embodiments, the method further comprises determining whether two or more variants are phased in cis or in trans based only on a sample obtained from a subject (i.e. without reference to a sample obtained from either parent of the subject). In some aspects, understanding if variants are phased in cis or in trans can inform risk assessment.[15]

In some embodiments, if the allele is a mutant form of succinate dehydrogenase complex, including subunits A, B, C or D and a pathogenic or likely pathogenic variant in SDHD is determined to be paternally inherited (i.e. to have a parent-of-origin of the father), the subject is periodically evaluated for paraganglioma or phaeochromocytoma and/or cascade genetic testing is initiated. If the allele is a mutant form of succinate dehydrogenase complex, including subunits A, B, C or D and a pathogenic or likely pathogenic variant in SDHD is determined to be maternally inherited (i.e. to have a parent-of-origin of the mother), no tumor screening may be necessary in an asymptomatic carrier and only cascade genetic testing is initiated.

In some embodiments, the method can be used to detect parent-of-origin of an aberrant methylation pattern in one or both of the determined haplotypes. For example, constitutional methylation of genes has been implicated in certain diseases, for example MLH1, MSH2, BRCA2 and numerous other genes have been implicated in cancers or disorders involving aberrant methylation.[61-64]

In some embodiments, the method further comprises predicting a similar pharmacogenomic outcome for a parent carrying a desirable or an undesirable haplotype, sub-haplotype or allele that has been detected in the subject, wherein the parent has been determined by evaluating the parent-of-origin of the desirable or undesirable haplotype, sub-haplotype or allele detected in the subject.

In some embodiments, the method further comprises determining if the allele is a disease risk-associated HLA haplotype, sub-haplotype or allele with a known parent-of-origin-effect, and if it is determined that the haplotype, sub-haplotype or allele is a disease risk-associated HLA haplotype, sub-haplotype or allele with a known parent-of-origin effect, periodically monitoring the subject for risk of disease based on the known parent-of-origin effect.

In some embodiments, the allele is an HLA haplotype, sub-haplotype or allele, and the method further comprises selecting a cancer vaccine or a cancer therapy for a parent of the subject based on a determination that the parent is the parent-of-origin of the HLA haplotype, sub-haplotype or allele in the subject.

In some embodiments, the method further comprises comparing a DNA sequence obtained from a sample at a crime scene with the haplotype, sub-haplotype or allele information and parent-of-origin information obtained from a subject, and if the DNA sequence obtained from the sample at the crime scene matches the DNA sequence of one of the haplotypes, sub-haplotypes or alleles from the subject, concluding that the identified parent-of-origin of the subject is associated with the crime scene.

In some embodiments wherein the haplotype, sub-haplotype or allele comprises an apparent de novo germline variant, wherein the biological parents of the subject test negative for the germline variant, the method further comprises determining parent-of-origin for the de novo germline variant to identify the parent with a potential risk for recurrence of the germline variant or to determine a risk to the parent of having a post-zygotic somatic mosaicism indicative of a risk of the parent developing disease.

In some embodiments, the method further comprises comparing haplotypes from two individuals having a corresponding mutation to identify a founder mutation by identifying a founder haplotype.

In some embodiments, the method further comprises administering a therapy to a parent determined to be the parent-of-origin of an undesirable haplotype, sub-haplotype or allele, wherein the therapy optionally comprises antisense oligonucleotides, an allele-specific targeting construct, or allele-specific gene editing targeted to the undesirable allele.

In some embodiments, the undesirable allele comprises a mutation implicated in a disorder with dominant negative effects, optionally as associated with an SNV, a copy number variant (CNV), an indel, methylation, or a triplicate repeat.

In some embodiments, the method can be used to provide improved structural variant characterization of haplotypes, including parent-of-origin structural variant information.[65,66]

In some embodiments, the method can be used to determine parent-of-origin of haplotypes which can be used for example to determine risk haplotype, to determine ancestry, or to examine complex traits.

In some embodiments, the method can be used to avoid a need for trio-based genotyping or trio-based sequencing to phase haplotypes to be used in studies to determine parent-of-origin effects, as is currently required.[67]

One specific embodiment of the invention implements the following steps:
  a) Acquire nanopore long reads and single-cell Strand-seq sequence data from a subject. Nanopore data is used to call variants, some of which are phased with Strand-seq in an inversion-aware manner. These phased variants are then used to phase the nanopore reads, which are used to phase more variants and DNA methylation in an iterative manner.
b) Without examining DNA methylation, Strand-seq and nanopore reads are combined to construct chromosome-length haplotypes, but the assignment of each homolog (i.e., chromosome-length haplotype) to haplotype 1 or 2 is random with respect to its Parent of Origin (PofO).
c), The DNA methylation status of iDMRs is used to identify the PofO for each chromosomal homolog.

In various other embodiments, apparatus and/or kits for carrying out the foregoing methods are provided. For example, in one embodiment, an apparatus is provided having a first sequencing apparatus for conducting a first sequencing technique to provide long-range phase information, a second sequencing apparatus for conducting a second sequencing technique to provide differential methylation status of at least one iDMR associated with the haplotype, sub-haplotype or allele, and a processor for analyzing the long-range phase information and the differential methylation status of the at least one iDMR to determine a parent-of-origin of the haplotype, sub-haplotype or allele associated with the haplotype. In one embodiment, a kit is provided having instructions for conducting a first sequencing technique to provide long-range phase information, instructions for conducting a second sequencing technique to provide differential methylation status of at least one iDMR associated with the haplotype, sub-haplotype or allel, and instructions for combining the long-range phase information and the differential methylation status of the at least one iDMR to determine a parent-of-origin of the haplotope, sub-haplotype or allele associated with the haplotype

EXAMPLES

Further embodiments are described with reference to the following examples, which are intended to be illustrative and not limiting in scope.

Example 1.0 Parent-of-Origin Detection and Chromosome-Scale Haplotyping Using Long-Read DNA Methylation Sequencing and Strand-Seq The inventors have integrated methylation-detecting nanopore sequencing with the long-range phase information in Strand-seq data to determine the parent-of-origin (PofO) of chromosome-length haplotypes for both DNA sequence and DNA methylation in five trios with diverse genetic backgrounds. The parent-of-origin was correctly inferred for all autosomes with an average mismatch error rate of 0.31% for SNVs and 1.89% for indels. Because the inventors' method can determine whether an inherited disease allele originated from the mother or the father, it can be soundly predicted that implementing this method will improve the diagnosis, treatment and management of many genetic diseases.

Figure 4:
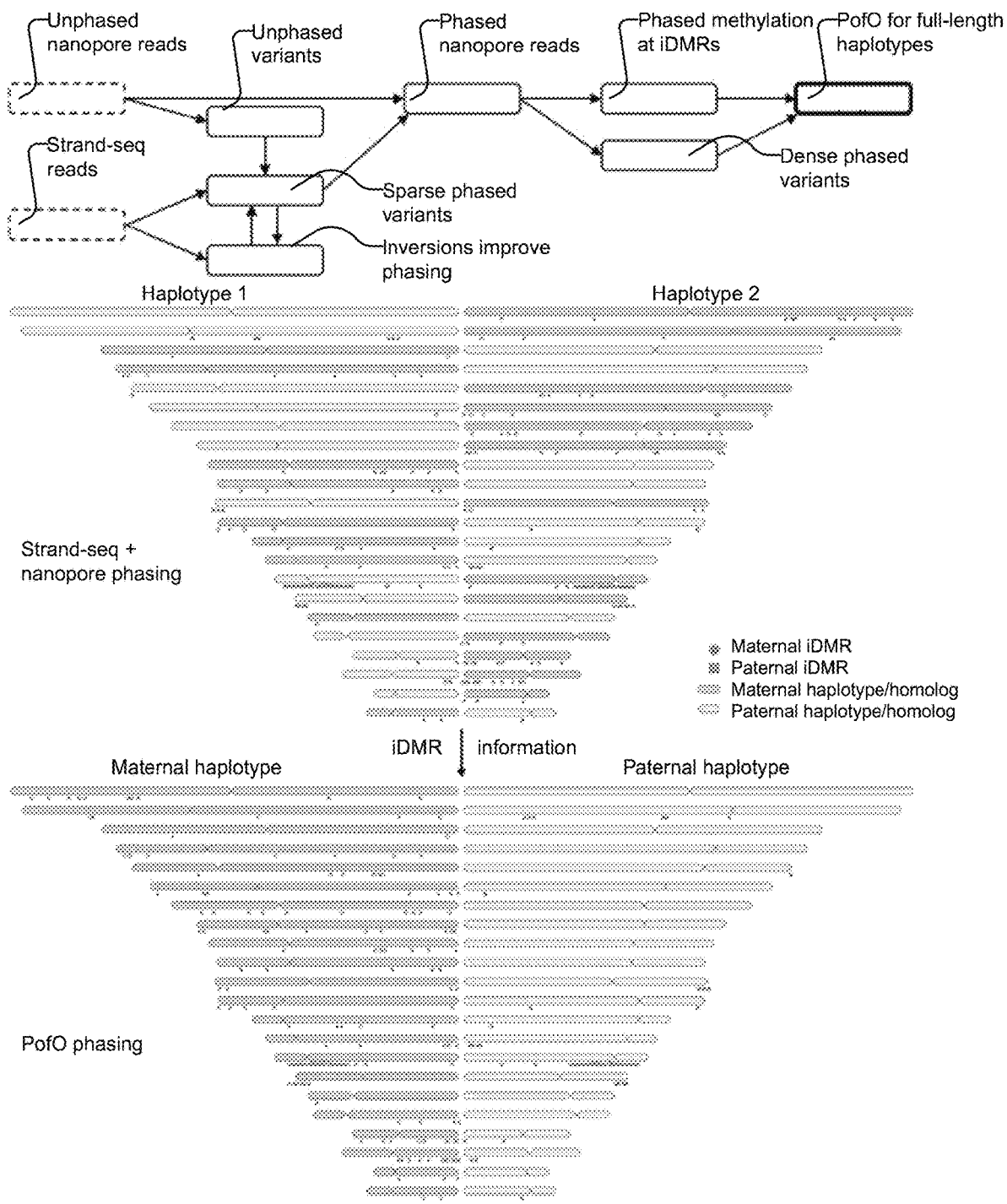
FIG. 4 shows an overview of the phasing method used in one example embodiment to determine parent-of-origin. The upper panel shows the workflow including inputs. The middle panel shows the combination of Strand-seq and nanopore reads to construct chromosome-length haplotypes, without the assignment of each homolog with respect to its parent-of-origin. The lower portion of the figure shows how iDMRs can be used to distinguish maternal and paternal homologs to assign parent-of-origin for each one of the chromosome-length haplotypes.

The Examples herein demonstrate that alleles along the full length of each autosome can be assigned to the maternal or paternal homolog when nanopore methylation and iDMRs are integrated with Strand-seq chromosome-length haplotypes (FIG. 4). This method does not require parental sequence data (trio information) or SNP linkage analysis but instead relies on the fact that all human autosomes have at least one imprinted differentially methylated region. The only input required is a sample of fresh whole blood or other viable cells that can be cultured. The inventors validated PofO assignment for heterozygous SNVs and indels against five gold standard trios from the Genome in a Bottle Consortium (GIAB), the Human Genome Structural Variation Consortium (HGSVC), and the 1000 Genomes Project (1KGP)[21-23]. By tracing pathogenic variants through families with sequencing efforts directed towards select family members, the described method has the potential to transform cascade genetic testing and improve screening for genetic disease.

Example 1.1—Nanopore and Strand-Seq Enable Chromosome Scale Haplotyping

The inventors used five human genomes to demonstrate the described approach including NA12878, HG002 and HG005 from GIAB, HG00733 from HGSVC, and NA19240 from 1 KGP[21-23]. For all the samples, the inventors used nanopore sequencing data at 24-38× depth of coverage and 42-220 Strand-seq libraries with 2.78-9.46× combined depth of coverage per sample. Nanopore raw signals were base-called and mapped to the human reference genome GRCh38 and SNVs and indels ("variants") were called from nanopore reads using Clair3[24].

While nanopore reads alone can be used to phase nearly all called variants for each sample, the resulting phase blocks are relatively short (N50 M±SD=4.85±3.66 Mb; "M" mean, "SD" standard deviation) and do not span full chromosomes (FIG. 5).

The inventors therefore applied inversion-aware Strand-seq phasing to the nanopore SNVs first and constructed sparse, chromosome-length haplotypes. Strand-seq phased 61.03%-95.02% of the common heterozygous SNVs between the ground truth and nanopore callsets with 0.14%-1.36% mismatch error rates (# of incorrectly phased variants/# of all phased variants), with each chromosome spanned by a single phase block (Table 1; FIG. 5). Strand-seq-phased SNVs were then used to phase nanopore reads (fraction of reads with at least MAPQ 20 that were successfully phased M±SD=71%±9.6%), which were in turn used to re-phase all variants and achieve dense, chromosome-scale haplotypes containing nearly all heterozygous SNVs and most indels (Table 1). Combining Strand-seq and nanopore in this way allowed the inventors to phase 99.37%-99.91% of the heterozygous SNVs and 96.29%-98.77% of the heterozygous indels that were present in both the ground truth and nanopore call sets with mismatch error rates 0.07%-0.54% for SNVs and 1.33%-2.43% for indels (Table 1).

Figure 5:
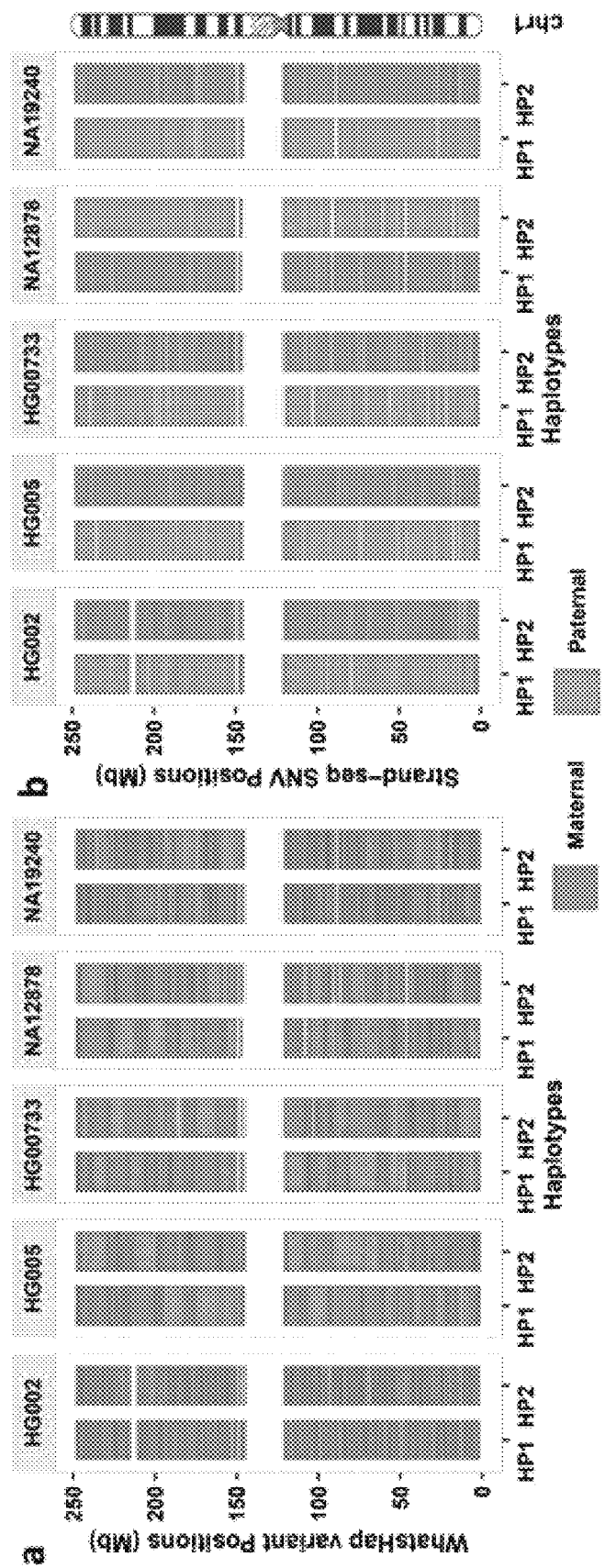
FIG. 5 shows a comparison of nanopore-only phasing and Strand-seq phasing. Panel (a) on the left shows subchromosomal nanopore phase blocks on chromosome 1. Panel (b) on the right shows the chromosome-scale haplotypes obtained by phasing nanopore-detected variants using Strand-seq for chromosome 1.

FIG. 5 shows a comparison of nanopore-only phasing and Strand-seq phasing. Panel (a) shows that subchromosomal nanopore phase blocks on chromosome 1 contain >99% of called SNVs and >96% of called indels. However, using nanopore-only phasing for PofO assignment results in per-chromosome M±SD=42.37%±7.13% PofO errors of SNVs and M±SD=42.82%+6.83% of indels. This is because arbitrary phase switches between phase blocks mean that PofO is effectively assigned at random for any phase block. WhatsHap v1.2.1 with the options—indels—ignore-read-groups was used to phase both indels and SNVs. Panel (b) shows that, by contrast, phasing nanopore-detected variants using Strand-seq results in chromosome-scale haplotypes with consistent PofO across each haplotype as shown here for chromosome 1.

FIG. 4 shows an overview of the PofO phasing method used in this example. The upper panel shows the inputs for the workflow are nanopore long reads and data from single-cell Strand-seq libraries. Nanopore data is used to call variants, some of which are phased with Strand-seq in an inversion-aware manner. These phased variants are then used to phase the nanopore reads, which are used to phase more variants and DNA methylation. Finally, the DNA methylation status of iDMRs is used to identify the PofO for each chromosomal homolog. The upper panel shows that, without examining DNA methylation, Strand-seq and nanopore reads can be combined to construct chromosome-length haplotypes, but the assignment of each homolog (i.e., chromosome-length haplotype) to HP1 or HP2 (haplotype 1 or haplotype 2) is random with respect to its PofO (upper portion of cartoon). However, as illustrated by the lower portion of the figure, iDMRs can be used to distinguish maternal and paternal homologs. Lollipops mark the locations of all 149 maternal iDMRs used in this study (methylated on the maternal homolog) and all 56 paternal iDMRs. For iDMR names and locations shown relative to cytobands, see Table 2.

TABLE 1

Phasing of heterozygous variants and comparison to the ground truth callset.

|  | HG002 | HG005 | HG00733 | NA12878 | NA19240 |
| --- | --- | --- | --- | --- | --- |
| Heterozygous SNVs |  |  |  |  |  |
| Total in ground truth callset | 2118417 | 1923279 | 2168512 | 2027669 | 2787148 |
| Common between nanopore and ground truth | 2100612 | 1916081 | 2071156 | 2009470 | 2688200 |
| Strand-seq switch rate | 0.0202 | 0.0078 | 0.0087 | 0.002 | 0.0055 |
| Strand-seq switch/flip rate | 0.0112 | 0.0044 | 0.0049 | 0.0012 | 0.003 |
| Strand-seq mismatch rate | 0.0136 | 0.006 | 0.0067 | 0.0014 | 0.0048 |
| Strand-seq # of correctly phased | 1496173 | 1516727 | 1255486 | 1906619 | 1903540 |
| Strand-seq # of incorrectly phased | 20560 | 9155 | 8457 | 2730 | 9239 |
| Combined Strand-seq & nanopore switch rate | 0.0016 | 0.0011 | 0.0027 | 0.0008 | 0.0029 |
| Combined Strand-seq & nanopore switch/flip rate | 0.001 | 0.0007 | 0.0016 | 0.0005 | 0.0016 |
| Combined Strand-seq & nanopore mismatch rate | 0.0054 | 0.0024 | 0.0034 | 0.0007 | 0.0035 |
| Combined Strand-seq & nanopore # of correctly phased | 2076204 | 1903642 | 2061700 | 2001412 | 2676235 |
| Combined Strand-seq & nanopore # of incorrectly phased | 11256 | 4634 | 7017 | 1489 | 9414 |
| Heterozygous Indels |  |  |  |  |  |
| Total in ground truth callset | 349059 | 264611 | 286492 | 312575 | 335801 |
| Common between nanopore and ground truth | 215894 | 195851 | 150941 | 186810 | 199359 |
| Combined Strand-seq & nanopore switch rate | 0.0409 | 0.0397 | 0.0237 | 0.0334 | 0.0323 |
| Combined Strand-seq & nanopore switch/flip rate | 0.0213 | 0.0206 | 0.0124 | 0.0172 | 0.0167 |
| Combined Strand-seq & nanopore mismatch rate | 0.0243 | 0.0218 | 0.0133 | 0.0174 | 0.0177 |
| Combined Strand-seq & nanopore # of correctly phased | 202815 | 184615 | 147100 | 178390 | 193356 |
| Combined Strand-seq & nanopore # of incorrectly phased | 5061 | 4106 | 1986 | 3161 | 3477 |

TABLE 2

Listing of Currently Known iDMRs.

| Chr | Start | End | Methylated Allele | Name | Reference |
| --- | --- | --- | --- | --- | --- |
| 1 | 11501432 | 11501606 | Maternal | PTCHD2 | Hernandez |
| 1 | 21292978 | 21293090 | Maternal | ECE1; LOC100506801 | Hernandez |
| 1 | 32471178 | 32471396 | Maternal | ZBTB8B | Joshi |
| 1 | 39515809 | 39516076 | Maternal | BMP8A | Akbari |
| 1 | 39558940 | 39560069 | Maternal | PPIEL, PABPC4 | Akbari, Court, Hernandez, Joshi, Zink |
| 1 | 68046745 | 68052008 | Maternal | DIRAS3, DIRAS3_Ex2, GNG12-AS1 | Akbari, Court, Hernandez, Joshi, Zink |
| 1 | 177032657 | 177032837 | Maternal | ASTN1 | Zink |
| 1 | 228315991 | 228316101 | Maternal | OBSCN | Joshi |
| 2 | 37535774 | 37536371 | Maternal | AC007391.3 | Akbari |
| 2 | 39243584 | 39244042 | Maternal | MAP4K3 | Hernandez |
| 2 | 94871304 | 94872050 | Paternal | TEKT4, AC097374.2 | Zink |
| 2 | 129587470 | 129587783 | Paternal | LOC151121 | Joshi |
| 2 | 131300169 | 131300522 | Maternal | FAR2P4, KLF2P4, PLEKHB2 | Zink |
| 2 | 131829505 | 131830210 | Paternal | C2orf27B | Joshi |
| 2 | 206249709 | 206274051 | Paternal | ZDBF2, GPR1-AS | Akbari, Court, Hernandez, Joshi, Zink |
| 2 | 206276199 | 206277222 | Paternal | ZDBF2 | Akbari |
| 2 | 209208321 | 209209864 | Maternal | MEAF6P1 | Zink |

TABLE 2-continued

Listing of Currently Known iDMRs.

| Chr | Start | End | Methylated Allele | Name | Reference |
|---|---|---|---|---|---|
| 2 | 232351651 | 232352102 | Maternal | ECEL1P3 | Akbari, Zink |
| 3 | 39501848 | 39502946 | Maternal | MOBP | Akbari, Hernandez, Zink |
| 3 | 192571221 | 192571834 | Maternal | FGF12 | Akbari, Zink |
| 4 | 6007986 | 6008636 | Maternal | C4orf50 | Akbari |
| 4 | 6104931 | 6106089 | Maternal | JAKMIP1 | Akbari, Hernandez, Joshi, Zink |
| 4 | 17641982 | 17642265 | Maternal | FAM184B | Zink |
| 4 | 88696886 | 88698218 | Maternal | NAP1L5, HERC3 | Akbari, Court, Hernandez, Joshi, Zink |
| 4 | 121932219 | 121933181 | Maternal | TRPC3 | Akbari, Hernandez, Zink |
| 4 | 154781458 | 154781987 | Maternal | RBM46 | Hernandez |
| 4 | 169774376 | 169774935 | Maternal | PTGES3P3 | Akbari, Zink |
| 5 | 563399 | 564627 | Paternal | MIR4456 | Akbari |
| 5 | 37208771 | 37209484 | Maternal | CPLANE1 | Akbari |
| 5 | 110726391 | 110727156 | Maternal | TMEM232 | Akbari |
| 5 | 117455047 | 117455203 | Maternal | LINC00992 | Hernandez |
| 5 | 136078784 | 136081177 | Maternal | VTRNA2-1 | Akbari, Hernandez, Joshi, Zink |
| 5 | 137889215 | 137889522 | Maternal | PKD2L2 | Hernandez |
| 5 | 138132931 | 138133533 | Maternal | NME5 | Akbari |
| 6 | 3848512 | 3850223 | Maternal | FAM50B, RP11-420L9.4 | Akbari, Court, Hernandez, Joshi, Zink |
| 6 | 29680602 | 29681316 | Maternal | ZFP57 | Hernandez |
| 6 | 31571958 | 31572360 | Maternal | LTA | Hernandez |
| 6 | 144006708 | 144009025 | Maternal | PLAGL1, HYMAI | Akbari, Court, Hernandez, Joshi, Zink |
| 6 | 158938903 | 158939474 | Paternal | RNU6-293P | Akbari |
| 6 | 160005233 | 160006715 | Maternal | IGF2R, AIRN | Akbari, Court, Hernandez, Joshi, Zink |
| 6 | 168384674 | 168384845 | Maternal | SMOC2 | Josh |
| 6 | 169654367 | 169655912 | Maternal | WDR27 | Akbari, Court, Hernandez, Joshi, Zink |
| 7 | 16850625 | 16851672 | Maternal | RP11-455J15.1 | Akbari, Zink |
| 7 | 23490379 | 23491453 | Maternal | RPS2P32 | Akbari, Joshi, Zink |
| 7 | 42856470 | 42857723 | Maternal | AC010132.10 | Akbari, Zink |
| 7 | 50781029 | 50783615 | Maternal | GRB10 | Akbari, Court, Hernandez, Joshi, Zink |
| 7 | 63926276 | 63926437 | Maternal | AC092634.8 | Akbari |
| 7 | 94656189 | 94658980 | Maternal | PEG10, SGCE | Akbari, Court, Hernandez, Joshi |
| 7 | 130489758 | 130494547 | Maternal | MEST, MESTIT1 | Akbari, Court, Hernandez, Joshi, Zink |
| 7 | 134831752 | 134832178 | Maternal | CALD1 | Zink |
| 7 | 138663807 | 138665288 | Maternal | SVOPL | Akbari, Hernandez, Joshi, Zink |
| 7 | 155070814 | 155072164 | Maternal | HTRSA, HTRSA-AS1 | Akbari, Court, Hernandez, Joshi, Zink |
| 8 | 2727694 | 2728686 | Maternal | LOC101927815 | Joshi |
| 8 | 2733559 | 2733944 | Maternal | LOC101927815 | Akbari, Joshi |
| 8 | 37747433 | 37748664 | Maternal | ERLIN2, LOC728024, CXORF56_pseudogene | Akbari, Court, Hernandez, Joshi |
| 8 | 39314503 | 39314602 | Maternal | ADAM5P | Hernandez |
| 8 | 60713696 | 60714534 | Maternal | CHD7 | Akbari, Joshi, Zink |
| 8 | 94119077 | 94120749 | Maternal | CDH17 | Akbari, Zink |
| 8 | 102527935 | 102530021 | Maternal | KB-1980E6.3 | Akbari, Zink |
| 8 | 140097560 | 140101293 | Maternal | TRAPPC9, PEG13 | Akbari, Court, Hernandez, Joshi, Zink |
| 8 | 140349118 | 140349831 | Maternal | TRAPPC9 | Akbari, Joshi |
| 8 | 143727780 | 143728612 | Maternal | FAM83H | Akbari |
| 9 | 41354506 | 41354931 | Maternal | CDRT15P6 | Akbari |
| 9 | 92098038 | 92098440 | Maternal | SPTLC1 | Akbari |
| 9 | 95312864 | 95313633 | Maternal | FANCC, FANCC_Int1-DMR | Akbari, Hernandez |
| 9 | 97574899 | 97575448 | Maternal | TMOD1 | Akbari |
| 9 | 113088975 | 113090248 | Maternal | AL449105.5 | Hernandez |
| 9 | 122225974 | 122226688 | Maternal | LHX6 | Akbari |
| 9 | 137416835 | 137418575 | Maternal | EXD3 | Akbari, Zink |
| 10 | 13158319 | 13158651 | Maternal | BTBD7P1 | Akbari |
| 10 | 27413523 | 27414618 | Maternal | PTCHD3 | Akbari, Hernandez |
| 10 | 97578421 | 97578764 | Maternal | ANKRD2 | Akbari |
| 10 | 119818422 | 119819215 | Maternal | INPP5F | Akbari, Court, Hernandez |
| 10 | 123991870 | 123992195 | Maternal | YBX2P1 | Akbari |
| 11 | 1997582 | 2003557 | Paternal | H19, H19/IGF2 | Akbari, Court, Hernandez |
| 11 | 2132351 | 2133882 | Paternal | IGF2_DMR2, IGF2, INS-IGF2 | Akbari, Court, Hernandez, Zink |
| 11 | 2145362 | 2149292 | Paternal | IGF2_DMR0, IGF2, IGF2-AS, INS-IGF2 | Akbari, Court, Hernandez, Zink |
| 11 | 2698551 | 2701309 | Maternal | KvDMR1, KCNQ1, KCNQ1OT1 | Akbari, Court, Hernandez, Zink |
| 11 | 7088807 | 7089387 | Maternal | RBMXL2 | Akbari, Hernandez, Zink |
| 11 | 132792877 | 132793069 | Maternal | OPCML | Hernandez |
| 11 | 133081592 | 133082483 | Maternal | OPCML | Akbari |

TABLE 2-continued

Listing of Currently Known iDMRs.

| Chr | Start | End | Methylated Allele | Name | Reference |
|---|---|---|---|---|---|
| 12 | 203429 | 204151 | Maternal | SLC6A12, RP11-28313.2 | Zink |
| 12 | 3838757 | 3839247 | Paternal | PARP11 | Akbari |
| 12 | 6444419 | 6444886 | Maternal | CD27, CD27-AS1, LOC678655 | Hernandez |
| 12 | 14773810 | 14774053 | Maternal | H2AFJ | Hernandez |
| 12 | 31117761 | 31120516 | Maternal | AC024940.1 | Akbari |
| 12 | 96223999 | 96224321 | Paternal | ELK3 | Hernandez |
| 12 | 130337741 | 130338059 | Maternal | PIWVIL1 | Hernandez |
| 13 | 20120765 | 20121239 | Maternal | GJA3 | Akbari |
| 13 | 48317165 | 48321834 | Maternal | RB1, PPP1R26P1 | Akbari, Court, Hernandez, Joshi, Zink |
| 13 | 48410208 | 48413428 | Maternal | LPAR6, RB1 | Akbari |
| 13 | 60267419 | 60269245 | Maternal | TARDBPP2 | Akbari, Hernandez, Zink |
| 13 | 99215482 | 99215886 | Paternal | UBAC2 | Akbari |
| 13 | 100975561 | 100975832 | Maternal | NALON-AS1 | Akbari |
| 14 | 33799699 | 33800646 | Maternal | NPAS3 | Akbari, Zink |
| 14 | 52269042 | 52269418 | Maternal | PTGDR | Akbari |
| 14 | 100726514 | 100726577 | Paternal | DLK1 | Joshi, Zink |
| 14 | 100807670 | 100811737 | Paternal | IG-DMR, MEG3, MEG3/DLK1 | Akbari, Court, Hernandez, Zink |
| 14 | 100823704 | 100828230 | Paternal | MEG3, AL117190.1 | Akbari, Court, Hernandez, Joshi, Zink |
| 14 | 100900401 | 100901267 | Maternal | MEG8, SNHG23 | Zink |
| 14 | 100904158 | 100905235 | Maternal | MEG8, SNHG23 | Akbari, Court, Hernandez, Zink |
| 14 | 106399075 | 106399179 | Maternal | IGHV3-37 | Hernandez |
| 15 | 23561842 | 23567348 | Maternal | MIR4508, MKRN3 | Akbari, Court, Hernandez, Joshi |
| 15 | 23606638 | 23609456 | Paternal | MKRN3 | Zink |
| 15 | 23629039 | 23629213 | Maternal | MKRN3 | Zink |
| 15 | 23634077 | 23634289 | Maternal | MKRN3 | Zink |
| 15 | 23642878 | 23643103 | Maternal | MAGEL2 | Zink |
| 15 | 23647089 | 23649052 | Maternal | MAGEL2 | Akbari, Court, Hernandez, Joshi, Zink |
| 15 | 23686274 | 23688131 | Maternal | NON | Akbari, Court, Hernandez, Joshi, Zink |
| 15 | 23797680 | 23798290 | Maternal | RNU6-741P | Zink |
| 15 | 23829311 | 23829706 | Paternal | RNU6-741P | Zink |
| 15 | 23854644 | 23855506 | Maternal | RP11-484P15.1 | Zink |
| 15 | 23857016 | 23861887 | Maternal | RP11-484P15.1 | Akbari, Zink, Zink |
| 15 | 23869152 | 23869962 | Maternal | RP11-484P15.1 | Akbari, Zink |
| 15 | 23877454 | 23878654 | Maternal | RP11-484P15.1 | Akbari, Zink |
| 15 | 23883075 | 23883432 | Paternal | RP11-484P15.1 | Zink |
| 15 | 23896280 | 23898594 | Maternal | PWRN4, RP11-484P15.1 | Akbari, Joshi, Zink |
| 15 | 23914065 | 23915807 | Paternal | RP11-484P15.1 | Zink |
| 15 | 23939735 | 23940870 | Paternal | RP11-484P15.1 | Zink |
| 15 | 24009020 | 24009903 | Paternal | PWRN4 | Zink |
| 15 | 24029218 | 24029630 | Paternal | PWRN4 | Zink |
| 15 | 24050087 | 24051502 | Paternal | PWRN4 | Zink |
| 15 | 24101056 | 24102058 | Maternal | SNRPN_intragenic_CpG32, PWRN2 | Akbari, Court, Zink |
| 15 | 24156357 | 24157105 | Paternal | PWRN2 | Zink |
| 15 | 24163134 | 24163879 | Paternal | PWRN2 | Zink |
| 15 | 24174217 | 24175175 | Paternal | PWRN2 | Zink |
| 15 | 24274859 | 24275806 | Paternal | RP11-58O11.2 | Zink |
| 15 | 24426478 | 24427725 | Maternal | SNRPN_intragenic_CpG29, PWRN3 | Akbari, Court, Zink |
| 15 | 24477606 | 24478059 | Maternal | SNRPN_intragenic_CpG30 | Akbari, Court |
| 15 | 24576113 | 24576926 | Paternal | PWRN1 | Zink |
| 15 | 24578494 | 24579011 | Paternal | PWRN1 | Zink |
| 15 | 24768838 | 24769820 | Paternal | PWRN1, SNRPN | Hernandez, Zink |
| 15 | 24772309 | 24773912 | Maternal | SNRPN_intragenic_CpG40, SNRPN | Akbari, Court, Hernandez, Joshi, Zink |
| 15 | 24823416 | 24824759 | Maternal | SNRPN | Akbari, Court, Hernandez, Joshi, Zink |
| 15 | 24846843 | 24848682 | Maternal | SNRPN, RP11-385H1.1 | Akbari, Court, Hernandez, Joshi, Zink |
| 15 | 24856474 | 24859220 | Maternal | SNRPN | Joshi, Zink |
| 15 | 24877552 | 24880264 | Maternal | SNRPN | Akbari, Court, Hernandez, Joshi, Zink |
| 15 | 24910643 | 24911281 | Paternal | SNRPN, AC090602.2 | Zink |
| 15 | 24951568 | 24957247 | Maternal | SNURF, SNRPN, RP11-701H24.9 | Akbari, Court, Hernandez, Joshi, Zink |
| 15 | 24957248 | 25001555 | Paternal | PWAR5, PWARSN, SNORD107, SNORD64, SNORD108, RP11-701H24.9, SNHG14 | Akbari, Joshi, Zink, Akbari, Zink |
| 15 | 25002560 | 25031118 | Paternal | SNHG14 | Akbari, Zink |
| 15 | 25038500 | 25057251 | Paternal | SNORD116Cluster, SNHG14 | Akbari, Joshi, Zink, Akbari, Zink |
| 15 | 25059478 | 25100741 | Paternal | SNORD116Cluster, SNHG14 | Akbari, Joshi, Zink, Akbari, Zink |

TABLE 2-continued

Listing of Currently Known iDMRs.

| Chr | Start | End | Methylated Allele | Name | Reference |
|---|---|---|---|---|---|
| 15 | 25141053 | 25144023 | Paternal | SNHG14 | Akbari |
| 15 | 25181244 | 25184030 | Paternal | SNORD115Cluster | Joshi, Zink |
| 15 | 29675828 | 29675992 | Maternal | AC022613.1 | Hernandez |
| 15 | 45022590 | 45022746 | Maternal | SORD | Hernandez, Joshi, Zink |
| 15 | 50909603 | 50909875 | Maternal | AP4E1 | Zink |
| 15 | 62344788 | 62345266 | Paternal | MIR6085 | Akbari |
| 15 | 81118252 | 81118870 | Paternal | CFAP161 | Akbari |
| 15 | 98865044 | 98867104 | Maternal | IGF1R | Akbari, Court, Hernandez, Joshi, Zink |
| 16 | 806879 | 808764 | Maternal | PRR25 | Akbari, Zink |
| 16 | 817075 | 818443 | Maternal | PRR25 | Akbari, Zink |
| 16 | 3254405 | 3254770 | Paternal | MEFV | Zink |
| 16 | 3295462 | 3295605 | Maternal | TIGD7 | Joshi |
| 16 | 3364669 | 3366488 | Paternal | MTRNR2L4, LA16c-306E5.2 | Akbari, Joshi, Zink |
| 16 | 3413769 | 3414262 | Paternal | LA16c-306E5.2 | Zink |
| 16 | 3431450 | 3441713 | Maternal | ZNF597, LA16c-306E5.2 | Akbari, Court, Hernandez, Joshi, Zink |
| 16 | 3442828 | 3444769 | Paternal | NAA60, ZNF597, LA16c-306E5.2 | Akbari, Court, Hernandez, Joshi, Zink |
| 17 | 4900360 | 4902310 | Maternal | CHRNE, C17orf107 | Akbari, Zink |
| 18 | 47667786 | 47668339 | Maternal | RP11-767C4.1 | Zink |
| 18 | 59969604 | 59969915 | Maternal | NFE2L3P1 | Akbari |
| 18 | 79616831 | 79617687 | Maternal | AC068473.4 | Akbari, Hernandez |
| 18 | 80147168 | 80149255 | Maternal | ADNP2, PARD6G-AS1 | Akbari, Zink |
| 19 | 4784658 | 4785523 | Maternal | MIR7-3HG | Akbari |
| 19 | 17323219 | 17324297 | Maternal | DDA1 | Akbari |
| 19 | 21082090 | 21082829 | Maternal | ZNF714 | Akbari |
| 19 | 36421856 | 36421978 | Paternal | AC092296.3 | Akbari |
| 19 | 38527504 | 38528578 | Maternal | RYR1, AC067969.1 | Zink |
| 19 | 38543705 | 38544472 | Maternal | RYR1 | Akbari, Zink |
| 19 | 53536955 | 53539153 | Maternal | ZNF331 | Akbari, Court, Hernandez, Zink |
| 19 | 53553367 | 53555638 | Maternal | ZNF331 | Akbari, Court, Hernandez, Zink |
| 19 | 56837125 | 56841903 | Maternal | PEG3, MIMT1, ZIM2, PEG3 | Akbari, Court, Hernandez, Zink |
| 19 | 56864809 | 56865037 | Maternal | MIMT1 | Zink |
| 19 | 58055058 | 58055675 | Paternal | ZSCAN1 | Zink |
| 20 | 31546686 | 31548526 | Maternal | HM13, MCTS2P | Akbari, Court, Hernandez, Joshi, Zink |
| 20 | 33667586 | 33668133 | Maternal | ACTL10, NECAB3 | Akbari |
| 20 | 37519751 | 37522258 | Maternal | BLCAP, NNAT | Akbari, Court, Hernandez, Joshi, Zink |
| 20 | 43513365 | 43516205 | Maternal | L3MBTL1 | Akbari, Court, Hernandez, Joshi, Zink |
| 20 | 48384392 | 48385349 | Maternal | RP1-66N13.1 | Akbari, Zink |
| 20 | 58836210 | 58847396 | Paternal | GNAS, GNAS-AS1 | Akbari, Court, Hernandez, Joshi, Zink |
| 20 | 58850116 | 58856591 | Maternal | GNAS-AS1, GNAS, GNAS-XL | Akbari, Court, Hernandez, Joshi, Zink |
| 20 | 58887966 | 58890443 | Maternal | GNAS_Ex1A, GNAS, LOC101927932 | Akbari, Court, Hernandez, Joshi, Zink |
| 20 | 59526001 | 59526478 | Maternal | RP11-164D18.2 | Zink |
| 20 | 63224686 | 63225146 | Maternal | AL096828.3 | Akbari |
| 20 | 63938417 | 63939470 | Maternal | UCKL1 | Akbari, Zink |
| 21 | 14063938 | 14064099 | Maternal | LIPI | Joshi |
| 21 | 39385480 | 39386798 | Maternal | WRB | Akbari, Court, Hernandez, Joshi, Zink |
| 21 | 46661115 | 46661858 | Maternal | PRMT2 | Akbari, Zink |
| 22 | 18609252 | 18609916 | Paternal | RIMBP3 | Akbari |
| 22 | 32043132 | 32043439 | Maternal | SLC5A1 | Akbari |
| 22 | 41681557 | 41683816 | Maternal | NHP2L1, SNU13 | Akbari, Court, Hernandez, Joshi, Zink |

Example 1.2—PofO Detection Using iDMRs

Figure 6:
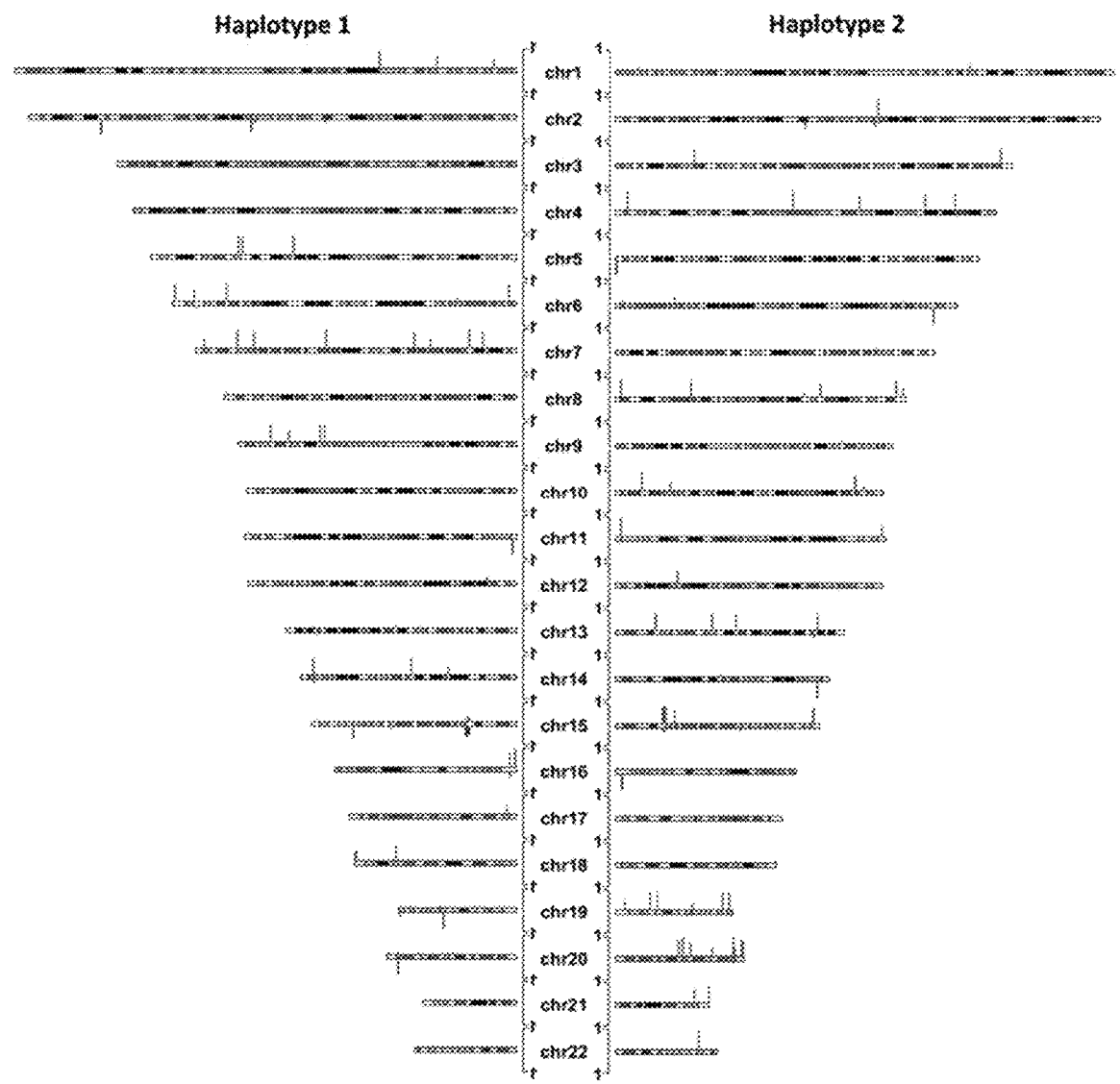
FIG. 6 shows CpG methylation at paternal and maternal iDMRs (extending upwardly) and paternal iDMRs (extending downwardly) in one example.

PofO-specific DNA methylation at iDMRs provides a unique source of information to determine the PofO of homologs, represented by chromosome-length haplotypes, without using parental sequence data. The inventors assembled a list of 205 iDMRs from previous genome-wide studies[25-29]. Chromosome X was ignored as it has no known iDMRs. The inventors combined DNA methylation information from phased nanopore reads with the known PofO information at the imprinted intervals to assign the PofO to each homolog. On average, 6 iDMRs (Median=5; SD=5.8; Range 1-32) were used for PofO assignment of each chromosome and each chromosome was assigned to its parental origin with an average of 96.3% confidence score (Median=99.2%; SD=6.4%; Range 60.7%-100%) (see FIG. 6 showing representative data for the CpG methylation data used for PofO assignment in HG0002; parallel data was obtained for HG005, HG00733, NA12878, and NA19240 but is not shown). On average, 6.9% of iDMRs conflicted with the majority PofO assignment. However, because iDMRs are weighted by the degree of differential methylation in each sample, conflicting iDMRs represented only 2.5% of the PofO contribution values (x as described in Example 1.4—Materials and Methods below).

FIG. 6 shows CpG methylation at paternal and maternal iDMRs used for parent of origin assignment in HG002. Maternally methylated iDMRs extend upward and paternally methylated iDMRs extend downward. Bars represent the fraction of CpGs with methylation difference ≥0.35 (differential methylation) between haplotypes (HP1–HP2 for haplotype 1 and HP2–HP1 for haplotype 2) at each iDMR for each haplotype.

Figure 7:
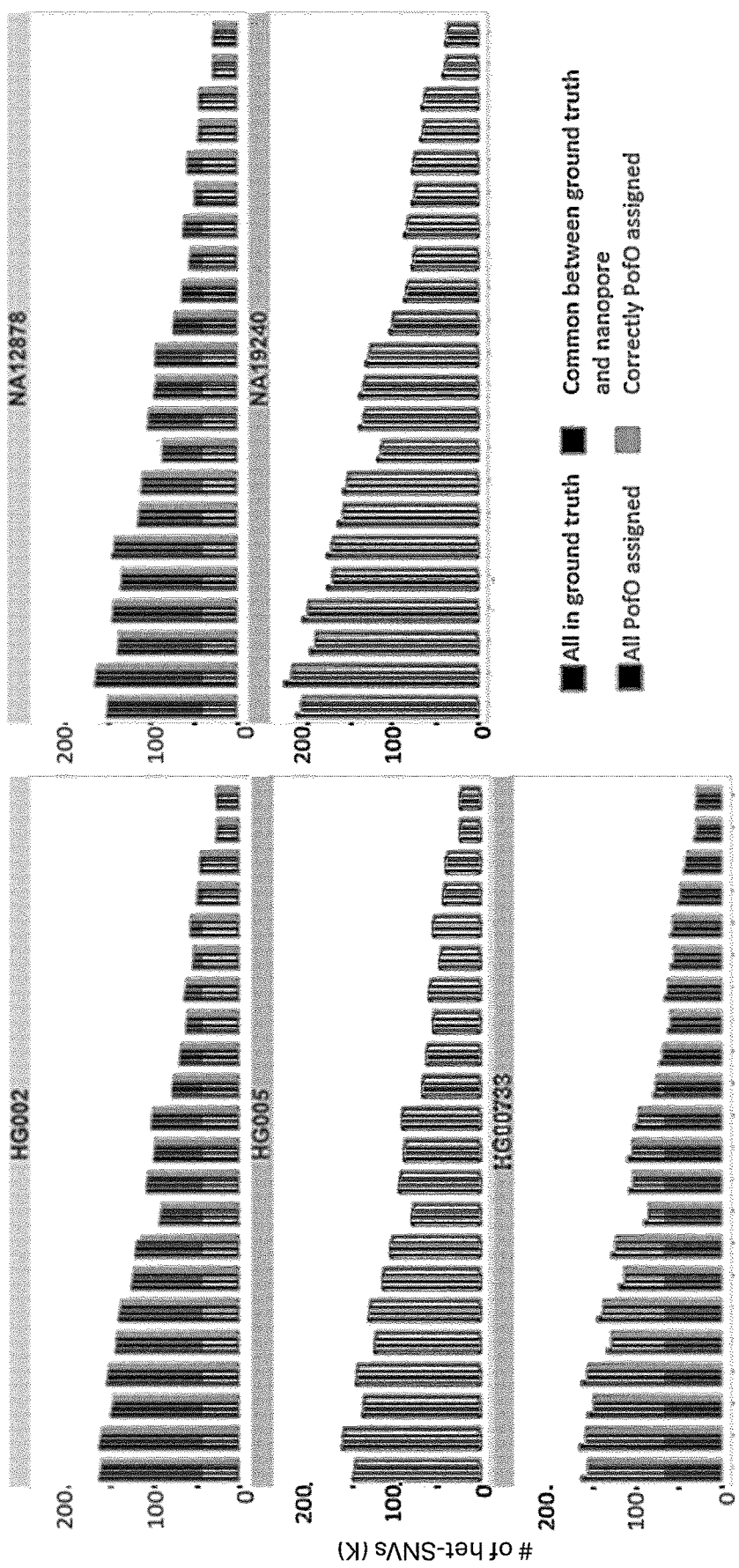
FIG. 7 shows the per-chromosome results for parent-of-origin assignment of het-SNVs in each of the five genomes examined in one example.

The inventors examined 220 autosomal homologs across 5 individuals in this study (5 individuals×22 autosomes×2 ploidy) and compared the inferred PofO with the trio-assigned PofO in the ground truth phased variant callsets. All the 220 homologs were correctly assigned PofO, that is, the chromosome-length haplotype was correctly identified as either maternal or paternal and had few phasing errors (chromosome-level mismatch error rates for SNVs: M±SD=0.34%±0.53%, range 0.03%-4.86% (FIG. 7); For indels: M±SD=1.93%±0.58%, range 0.98%-5.35%). FIG. 7 shows per-chromosome results for PofO assignment of heterzygous SNVs in each of the five individuals for chromosomes 1-22 represented from left to right. PofO could be assigned to all homologs. Bars indicate from left to right (i) all heterozygous SNVs in ground truth; (ii) common het-SNVs between ground truth and nanopore; (iii) het-SNVs with PofO assigned, and (iv) het-SNVs with correct PofO assigned. The small fraction of variants with incorrect PofO are sporadic phasing errors in the Strand-seq or nanopore data.

For additional confirmation that PofO phasing extracts reliable parental information, the inventors calculated Mendelian error rates between each child's inferred parental haplotypes and ground truth variant genotypes for their parents. For the HG005 genome, Mendelian error rates for maternal-mother and paternal-father comparisons were low (M±SD=0.27%±2.69%; calculated for non-overlapping bins of 1000 variants), while they were high for maternal-father and paternal-mother comparisons (representing misassigned PofO; M±SD=25.75%±14.14%). For maternal-mother and paternal-father comparisons, the highest mean error rate for any chromosome was 2.29%, for chromosome 8 in HG002. This is less than one-eighth of the lowest mean error rate for any chromosome in maternal-father and paternal-mother comparisons (19.69% for chromosome 21 in NA12878), suggesting that PofO assignment is correct for all chromosomes. Similar results were demonstrated for Mendelian error rates for the HG002, HG00733, NA19240 and NA12878 genomes.

Example 1.3—Analysis of Experimental Data

The experiments described herein show that chromosomal homologs, represented by chromosome-length haplotypes of SNVs and indels, can be assigned PofO without using parental sequence data. Long nanopore reads provide DNA sequence information along with PofO information in the form of DNA methylation differences between maternal and paternal alleles at known iDMRs. Strand-seq libraries provide sparse global haplotype information that phases variants and nanopore reads to reconstruct individual homologs. The PofO of each homolog can then be determined based on the consensus of one or more embedded iDMRs (FIG. 4).

PofO phasing has the potential to address immediate clinical needs in the diagnosis and management of genetic disease. These include improving variant curation and estimates of disease penetrance through co-segregation of variants to each side of the family with and without relevant disease phenotypes, determining which parent may have a risk for mosaicism in the context of a de novo variant, and establishing appropriate screening recommendations for pathogenic variants in genes with known PofO effects—as seen with SDHD and SDHAF2. Furthermore, PofO phasing provides a considerable advantage over current clinical testing in facilitating cascade genetic testing that allows opportunities for intervention in actionable genetic diseases[31]. Contacting, counseling and testing relatives is a significant logistical and financial burden to patients and healthcare systems, especially when considering adult-onset conditions, where testing of parents is frequently not possible. Cascade genetic testing may be hindered by limited intrafamily communication and fractured family structures, and has low uptake in ethnic minority populations[20]. PofO phasing stands to enable focused approaches to cascade genetic testing throughout families, bringing goals of optimal cascade genetic testing rates within reach[32]. Of importance, the ability of PofO phasing to infer the pathogenic variant status of a patient's parent with a high degree of certainty is likely to place an even greater emphasis on the duty to warn at-risk individuals of actionable genomic findings that may have been primarily or secondarily sought throughout the course of genetic testing. Similar issues are already familiar to clinical genetics in the setting of obligate carriers, but because this approach need only test a single person to reconstruct the complete genomic contribution from each parent, there will be ethical considerations if PofO phasing is integrated into mainstream clinical genetic testing due to the unprecedented scale.

The inventors used a well-validated set of known iDMRs. These iDMRs are reported in at least two studies or confirmed in 179 WGBS datasets from 119 blood and 60 tissue samples. Using this set of iDMRs, the inventors were able to assign PofO for all the tested samples in all autosomes. Even though the paternal or maternal origin of methylation at iDMRs is consistent whenever just one allele is methylated, imprinted methylation can be variable in the sense that the two parental alleles may have similar amounts of DNA methylation in some tissues and individuals[27,33]. This may result in inability to assign PofO in some chromosomes in some individuals. However, excepting chromosome 17 which has a single iDMR and chromosome 2 which has two, all autosomes have at least three iDMRs, which should enable PofO assignment even in presence of limited inter-individual and inter-tissue variability. In principle, this redundancy also makes PofO phasing more robust to epimutation and genomic imprinting disorders that might alter DNA methylation at iDMRs[34].

Moreover, in a few iDMRs in some samples, such as maternally methylated TRPC3 at chromosome 4 in NA12878, the inventors detected hypermethylation on the allele that is reported to be unmethylated. This explains the low confidence score for PofO assignment for a few chromosomes, such as chromosome 4 in NA12878 with the lowest confidence score (60.7%). Such discrepancies might be due to inaccuracies in methylation calling or phasing of nanopore reads, or could reflect random allelic DNA methylation. Improvement of the current iDMR list will potentially reduce such errors in the future. DNA methylation-based (canonical) imprinting has been described in all placental mammals, and genomic maps of iDMRs have been established for a number of species, notably mice and primates[7,35-37]. Therefore, the approach described herein can potentially be expanded to other mammals.

Even when a homolog is assigned the correct PofO overall, local phasing errors can cause incorrect PofO assignment for some variants. The chromosome-length haplotypes constructed in the examples described herein are highly accurate, however, with mean mismatch error rates of 0.31% for SNVs and 1.89% for indels. Although the inventors identified only 61.3% of the indels in the ground truth dataset, this reflects a limitation of current nanopore technology and could be improved with the addition of short Illumina readsa[38]. The inventors observed rare switch errors for SNVs and indels primarily at centromeres and at inversions (e.g. an inversion on chromosomes 8 in HG002 caused the largest mismatch error rates; FIG. 7), but these generally contain few variants. Phasing errors at centromeres are likely due to misaligned reads in repetitive sequences, while errors at inversions are due to changes in sequence orientation that disrupt the directional information Strand-seq exploits for phasing[8]. Inversion-related phasing errors can be partially addressed with a new StrandPhaseR function that re-phases variants inside known inversions[39]. This is essential when iDMRs fall inside inversions, where they may support the wrong PofO if phasing is not corrected (e.g. iDMRs RIMBP3 and CDRT15P6), or when genes of interest fall inside inversions (e.g., PMS2 in inversion chr7: 5850673-6795880).

Sequencing costs for PofO phasing are relatively low, with as little as 24× nanopore and 3× Strand-seq coverage used in the examples described herein. The DNA methylation information that underlies PofO assignment is robust and can easily be extracted from nanopore sequence data, while formerly-rare Strand-seq libraries can now be produced in large numbers (>1000) at a reduced cost[40]. In principle, genomic regions that are identical by descent in distant relatives could also be leveraged to partially assign PofO with large SNV datasets, using either the sex chromosomes or the ethnicity of the parents, but such bioinformatic approaches would require that parents differ substantially in genetic background and would be subject to well-known ethnic biases in genomic datasets[41]. Given the simplicity and accuracy of PofO phasing, the lack of trio-free alternatives at present for extracting PofO information from genomic data, and the method's remarkable clinical applications, PofO phasing has the potential to become a routine component of genomic analysis.

Example 1.4—Overview of Experimental Techniques

Nanopore Sequencing and Data

The inventors sequenced native DNA from an Ashkenazi son (GM24385 or HG002) at 32-fold coverage on a nanopore PromethION instrument using a library preparation and sequencing protocol described previously[6]. In addition to HG002, the inventors used public nanopore data for HG005, HG00733, NA12878 and NA19240. Raw nanopore fast5 files for HG005 and HG00733 were downloaded from the Human Pangenome Reference Consortium[42]; NA12878 was obtained from Jain et al. 201843; and NA19240 from De Coster et al. 201944. For HG002, HG005 and NA12878, paternal and maternal variant data and ground truth phased variants were obtained through GIAB v4.2.1, and for NA19240 and HG00733 parental phased variants were obtained from 1 KGP shapeit2 v2a[22,23].

Nanopore Data Analysis

Basecalling and mapping: Nanopore signal-level data were basecalled using Oxford Nanopore Technologies guppy basecaller version 6.0.1 and the super accuracy model (dna_r9.4.1_450bps_sup) with default settings. Basecalled nanopore reads were mapped to the human reference genome (GRCh38) using minimap2 version 2.24 with the -MD and -L options selected[45].

Variant calling: Upon alignment, Clair3 version 0.1-r10 with trained model r941_sup_g5014 and default settings was used to call variants from nanopore alignment data[24]. High quality variant calls (marked as "PASS" by the software) from Clair3 were then used for Strand-seq phasing (see the next section).

Methylation calling: To call DNA methylation and obtain per-read CpG methylation information from nanopore data, the inventors used nanopolish version 13.3 with default settings[5]. Per-read methylation call data were then preprocessed using NanoMethPhase v1.0 with—callThreshold 1.5 parameter for downstream analysis and PofO phasing[6,46].

Strand-Seq Data Processing, Phasing, and Inversion Correction

The inventors obtained 45 public Strand-seq libraries for HG005 and 66 for HG002 from GIAB[22,47] and 230 libraries for HG00733 and 234 libraries for NA19240 from HGSVC[21]. The inventors used the 96 high-depth OP-Strand-seq libraries for NA12878 described previously (clusters 5 and 6)[40].

The inventors trimmed adapters from paired-end FASTQ files and removed short reads (<30 bp) and low-quality bases (<15) with Cutadapt[48]. The inventors used Bowtie2 to align reads to the GRCh38 human reference genome and discarded reads that had MAPQ less than 10 or that did not map to chromosomes 10-22, X, and Y[49]. The inventors used Picard (from the Broad Institute of MIT and Harvard, available on GitHub) to mark duplicate reads and then ran ASHLEYS QC with default settings and window sizes 5000000, 2000000, 1000000, 800000, 600000, 400000, and 200000 to discard libraries with a Strand-seq quality score below 0.5[50].

The inventors ran BreakpointR (commit 58cce0b09d01040892b3f6abf0b11caeb403d3f5 of BreakpointR from daewoooo of the Department of Genome Sciences at the University of Washington, available on GitHub) with background set to 0.1, chr set to the autosomes, and maskRegions set to a previously described blacklist[30,51]. The inventors used 8 Mb bins because it was found they linked phasing across difficult regions such as inversions more readily and prevented large switch errors. The inventors used the function exportRegions with default settings to identify regions of the genome with both Watson and Crick reads that are suitable for phasing. The inventors phased biallelic heterozygous SNVs called from the nanopore data for each sample using StrandPhaseR with num.iterations set to 3, with splitPhasedReads and assume.biallelic set to TRUE, with R v4.0.5, and with v1.0.1 or higher of the dependency rlang (commit bb19557235de3d82092abdc11b3334f615525b5b of the devel branch of StrandPhaseR from daewoooo of the Department of Genome Sciences at the University of Washington, available on GitHub)[11].

Inversions disrupt Strand-seq's directional phase information. The inventors called inversions for each sample using the R package InvertypeR (commit a5fac3b6b8264db28de1a997ad0bc062badea883 of InvertypeR/commits/main from vincent-hanlon, available on GitHub)[51]. In brief, the inventors used the nanopore SNVs to create a pair of composite files for each sample, with the addition of the genomic coordinates chr8:8231088-12039415 in the blacklist to ensure that the common large inversion at those coordinates was correctly represented. The inventors genotyped a catalog of published inversion coordinates with adjust_method set to 'all' and with priors as previously described, as well as a list of de novo sample-specific strand switches identified by running BreakpointR three times on the composite files with different bin sizes[30, 51]. For the latter, the inventors used prior probabilities of 0.9, 0.05, and 0.05 for reference, heterozygous, and homozygous genotypes, respectively. The inventors combined inversions with posterior probabilities above 0.95 from the two callsets by discarding any inversions from the catalog callset that intersected the de novo callset (bedtools intersect -v -r -f 0.1). The inventors did not remove misoriented reference contigs, which appear as homozygous inversions in all samples, because they disrupt phasing in the same way that inversions do.

The function correctInvertedRegionPhasing in the StrandPhaseR package switches the phase of heterozygous SNVs within homozygous inversions and re-phases SNVs within heterozygous inversions[39]. The inventors used sample-specific inversion calls larger than 10 kb along with the nanopore sample-specific SNV positions, recall.phased and assume.biallelic set to TRUE, het.genotype set to 'lenient', lookup.bp set to 1000000, background set to 0.1, and lookup.blacklist set to the blacklist above. The resulting chromosome-length inversion-corrected SNV haplotypes were used to phase nanopore reads relative to each other.

iDMRs, Chromosome-Scale Haplotypes, and PofO Detection

Validation of iDMRs

The inventors gathered the list of previously reported iDMRs from five prior genome-wide studies[25-29]. iDMRs with overlap between 2 or more studies were merged. This resulted in 102 merged iDMRs and 326 iDMRs reported in only a single study. The inventors previously surveyed imprinted methylation genome-wide using 12 nanopore-sequenced cell lines with their trio sequencing information from 1 KGP[29]. The inventors used the same cell lines to examine the 326 iDMRs from a single study, above. For each CpG site with a coverage of >4 within the iDMRs, methylation frequency (the fraction of reads methylated at a CpG) was calculated. The inventors then calculated the difference between average methylation frequencies for the paternal and maternal alleles for each iDMR in each cell line. Ninety-four iDMRs with |methylation difference| 0.25 between alleles and with conflicting PofO between any of the 12 cell lines and the corresponding prior study were excluded. To further validate the 232 remaining iDMRs reported in a single study, the inventors used WGBS datasets for 119 blood samples from 87 individuals in the Blueprint consortium and 60 tissue samples for 29 tissue types in ENCODE and the RoadMap consortium[52-54]. At iDMRs only one allele is methylated, therefore, the aggregated methylation frequency from both alleles at these regions is expected to be ~50% (partial methylation). Thus, the inventors examined partial methylation at the 232 iDMRs in the WGBS datasets. For each WGBS sample, the inventors used CpGs with at least 5 mapped WGBS reads and at each iDMR the number of CpGs with partial methylation (methylation frequency between 0.35-0.65 among mapped reads) was counted. An iDMR is then considered partially methylated if it had at least 5 CpGs in the WGBS sample and more than 60% of the CpGs showed partial methylation. Out of the 232 iDMRs, 129 iDMRs were excluded because they were partially methylated in less than two blood or tissue samples or in less than 5% of blood or tissue samples in which the iDMR could be examined (i.e., the iDMR had at least 5 CpGs with a coverage of ≥5). Overall, the inventors gathered a list of 205 known iDMRs of which 102 were reported in multiple studies and 103 (out of 326) were reported in a single study, the most certain of which are listed in Table 2.

Determination of Parent-of-Origin

The inventors then integrated several steps to detect chromosome-scale haplotypes with their PofO as follows:

1. Strand-seq phasing demonstrates sparse chromosome-scale haplotypes. Phased SNVs from Strand-seq were used to phase nanopore reads to either HP1 or HP2 haplotypes. A minimum mapping quality of 20 and base quality of 7 was used to tag each read with the phased SNVs. A read is tagged as HP1 if it has at least one phased SNV from HP1 with a ratio (Number of SNVs from HP1 that mapped to the read/All phased SNVs that mapped to the read) 0.75, and vice versa.

2. Phased nanopore reads from step 1 were then used to re-phase all the variants (SNVs and indels) to each haplotype. At least 2 phased reads are needed to support a variant to assign it as HP1 or HP2.

3. Nanopore reads were then phased a second time using all the phased variants from step 2 with the conditions mentioned in step 1.

4. Per-read methylation information for each nanopore read at known iDMRs were extracted and integrated to its phase information from step 3. This enabled the inventors to phase each CpG methylation in each read to either HP1 or HP2 and calculate the methylation frequency (# of methylated reads/# of all reads) at each CpG site for each haplotype. Methylation frequencies were then used to assign haplotypes to their PofO for each sample as follows:

At each of the 205 known iDMRs the inventors counted CpGs with ≥0.35 difference in methylation frequency between haplotypes (differential methylation). The inventors then calculated the contribution value of the iDMR to the PofO detection of each haplotype as follows:

$$x = ma/n$$

Where m is the average methylation frequency for the haplotype, a is the number of differential methylated CpGs that support PofO for the haplotype, and n is the number of all CpGs at the iDMR. Only iDMRs with more than 10 detected CpGs and with $|a_{(HP1)} - a_{(HP2)}|$ comprising at least 10% of all detected CpGs were considered for PofO assignment. As an example, for a maternally methylated iDMR with 20 CpGs and 0.8 average methylation frequency at HP1 and 0.3 at HP2 if 12 CpGs show ≥0.35 methylation in HP1 compared to HP2 and 2 CpGs show ≥0.35 methylation in HP2 compare to HP1 then:

x for HP1 as maternal and HP2 as paternal is x=0.8×12/20 and x for HP1 as paternal and HP2 as maternal is x=0.3×2/20.

On each chromosome for each haplotype as being maternal or paternal, the value of X=Σx will be:

$$X = \sum_{j=1}^{k} m_j a_j / n_j$$

Where k is the number of iDMRs considered for the chromosome. If X for HP1 as maternal (which is the same as X for HP2 as paternal) be greater than X for HP2 as maternal (which is the same as X for HP1 as paternal) then HP1 is the maternal and HP2 is the paternal origin and vice versa. Moreover, if for example HP1 assigned as the maternal and HP2 as the paternal homolog, the inventors calculated the confidence score for PofO assignment as $X_{(HP1\ maternal)}/(X_{(HP1\ maternal)}+X_{(HP2\ maternal)})$ or $X_{(HP2\ paternal)}/(X_{(HP2\ paternal)}+X_{(HP1\ paternal)})$.

5—Finally, phased variants from step 2 were assigned to their PofO with the results from step 4.

All the steps are integrated into a workflow and tool, PatMat, and the instructions are provided on GitHub (available as PatMat from vahidAK).

Mendelian Errors

To verify the PofO assignments, the inventors calculated the frequency of one kind of Mendelian error between the PofO-assigned haplotypes and the genotypes of the parents. The inventors obtained genotypes from GIAB for the parents of HG002 and HG005 (v4.2.1), from 1KGP for the parents of HG00733 and NA19240 (v2a), and from Byrska-Bishop et al. 2021 for the parents of NA12878[22,23,47,55]. For each parent-child pair, the inventors examined loci at which they found a phased heterozygous genotype for the child and either a heterozygous or homozygous alternate genotype for the parent. Where the child had a maternal reference allele and the mother was homozygous alternate, the inventors called a Mendelian error (similarly for the child's paternal allele and the father's genotype). The inventors did this for non-overlapping bins of 1000 variants and calculated the error rate as the number of such Mendelian errors divided by the number of variants examined. The inventors plotted the resulting error rates on chromosomes using RIdeogram[56].

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

For example, although various example embodiments have been described with reference to determining chromosome-length haplotypes, and it is believed without being bound that determining chromosome-length haplotypes will yield the most accurate results, smaller portions of sequence data could in alternative embodiments be assembled to generate at least a partial haplotype so long as at least a few variants associated with an iDMR are captured so as to allow both the haplotype of the allele of interest and a methylation status of an iDMR associated with that allele to be determined to determine parent-of-origin for that allele.

REFERENCES

The following references are of interest to the subject matter described herein. Each of the following references is incorporated by reference herein in its entirety.

1. Zheng, G. X. Y. et al. Haplotyping germline and cancer genomes with high-throughput linked-read sequencing. *Nat. Biotechnol.* 34, 303-311 (2016).
2. Wenger, A. M. et al. Accurate circular consensus long-read sequencing improves variant detection and assembly of a human genome. *Nat. Biotechnol.* 37, 1155-1162 (2019).
3. Cheng, H. et al. Haplotype-resolved assembly of diploid genomes without parental data. *Nat. Biotechnol.* (2022) doi:10.1038/s41587-022-01261-x.
4. H., L. A. et al. Detection and mapping of 5-methylcytosine and 5-hydroxymethylcytosine with nanopore MspA. *Proc. Natl. Acad. Sci.* 110, 18904-18909 (2013).
5. Simpson, J. T. et al. Detecting DNA cytosine methylation using nanopore sequencing. *Nat. Methods* 14, 407 (2017).
6. Akbari, V. et al. Megabase-scale methylation phasing using nanopore long reads and NanoMethPhase. *Genome Biol.* 22, 68 (2021).
7. Gigante, S. et al. Using long-read sequencing to detect imprinted DNA methylation. *Nucleic Acids Res.* 47, e46-e46 (2019).
8. Porubský, D. et al. Direct chromosome-length haplotyping by single-cell sequencing. *Genome Res.* 26, 1565-1574 (2016).
9. Selvaraj, S., R Dixon, J., Bansal, V. & Ren, B. Whole-genome haplotype reconstruction using proximity-ligation and shotgun sequencing. *Nat. Biotechnol.* 31, 1111-1118 (2013).
10. Falconer, E. et al. DNA template strand sequencing of single-cells maps genomic rearrangements at high resolution. *Nat. Methods* 9, 1107-1112 (2012).
11. Porubsky, D. et al. Dense and accurate whole-chromosome haplotyping of individual genomes. *Nat. Commun.* 8,1293 (2017).
12. Porubsky, D. et al. Fully phased human genome assembly without parental data using single-cell strand sequencing and long reads. *Nat. Biotechnol.* 39, 302-308 (2021).
13. Van Der Mey, A. L., Maaswinkel-Mooy, P., Cornelisse, C., Schmidt, P. & Van De Kamp, J. P. GENOMIC IMPRINTING IN HEREDITARY GLOMUS TUMOURS: EVIDENCE FOR NEW GENETIC THEORY. *Lancet* 334, 1291-1294 (1989).
14. Knowles, J. W., Rader, D. J. & Khoury, M. J. Cascade Screening for Familial Hypercholesterolemia and the Use of Genetic Testing. *JAMA* 318, 381-382 (2017).
15. Richards, S. et al. Standards and guidelines for the interpretation of sequence variants: a joint consensus recommendation of the American College of Medical Genetics and Genomics and the Association for Molecular Pathology. *Genet. Med.* 17, 405-424 (2015).
16. Hensen, E. F. et al. Somatic loss of maternal chromosome 11 causes parent-of-origin-dependent inheritance in SDHD-linked paraganglioma and phaeochromocytoma families. *Oncogene* 23, 4076-4083 (2004).
17. Huai-Xiang, H. et al. SDH5, a Gene Required for Flavination of Succinate Dehydrogenase, Is Mutated in Paraganglioma. *Science* (80-.). 325, 1139-1142 (2009).
18. Hampel, H. Genetic counseling and cascade genetic testing in Lynch syndrome. *Fam. Cancer* 15, 423-427 (2016).
19. Lee, P. W. C. et al. Evaluating the impact of universal Lynch syndrome screening in a publicly funded healthcare system. *Cancer Med.* 9, 6507-6514 (2020).
20. Braley, E. F. et al. Patient ethnicity and cascade genetic testing: a descriptive study of a publicly funded hereditary cancer program. *Fam. Cancer* (2021) doi:10.1007/s10689-021-00270-0.
21. Chaisson, M. J. P. et al. Multi-platform discovery of haplotype-resolved structural variation in human genomes. *Nat. Commun.* 10, 1784 (2019).
22. Zook, J. M. et al. An open resource for accurately benchmarking small variant and reference calls. *Nat. Biotechnol.* 37, 561-566 (2019).
23. Auton, A. et al. A global reference for human genetic variation. *Nature* 526, 68-74 (2015).

24. Zheng, Z. et al. Symphonizing pileup and full-alignment for deep learning-based long-read variant calling. *bioRxiv* 2021.12.29.474431 (2021) doi:10.1101/2021.12.29.474431.
25. Court, F. et al. Genome-wide parent-of-origin DNA methylation analysis reveals the intricacies of human imprinting and suggests a germline methylation-independent mechanism of establishment. *Genome Res.* 24, 554-569 (2014).
26. Joshi, R. S. et al. DNA Methylation Profiling of Uniparental Disomy Subjects Provides a Map of Parental Epigenetic Bias in the Human Genome. *Am. J. Hum. Genet.* 99, 555-566 (2016).
27. Zink, F. et al. Insights into imprinting from parent-of-origin phased methylomes and transcriptomes. *Nat. Genet.* 50, 1542-1552 (2018).
28. Hernandez Mora, J. R. et al. Characterization of parent-of-origin methylation using the Illumina Infinium MethylationEPIC array platform. *Epigenomics* 10, 941-954 (2018).
29. Akbari, V. et al. Genome-Wide Detection of Imprinted Differentially Methylated Regions Using Nanopore Sequencing. *bioRxiv* 2021.07.17.452734 (2021) doi: 10.1101/2021.07.17.452734.
30. Porubsky, D. et al. breakpointR: an R/Bioconductor package to localize strand state changes in Strand-seq data. *Bioinformatics* 36, 1260-1261 (2020).
31. Miller, D. T. et al. ACMG SF v3.0 list for reporting of secondary findings in clinical exome and genome sequencing: a policy statement of the American College of Medical Genetics and Genomics (ACMG). *Genet. Med.* 23, 1381-1390 (2021).
32. Offit, K. et al. Cascading After Peridiagnostic Cancer Genetic Testing: An Alternative to Population-Based Screening. *J. Clin. Oncol.* 38, 1398-1408 (2020).
33. Prickett, A. R. & Oakey, R. J. A survey of tissue-specific genomic imprinting in mammals. *Mol. Genet. Genomics* 287, 621-630 (2012).
34. Monk, D., Mackay, D. J. G., Eggermann, T., Maher, E. R. & Riccio, A. Genomic imprinting disorders: lessons on how genome, epigenome and environment interact. *Nat. Rev. Genet.* 20, 235-248 (2019).
35. Renfree, M. B., Hore, T. A., Shaw, G., Marshall Graves, J. A. & Pask, A. J. Evolution of Genomic Imprinting: Insights from Marsupials and Monotremes. *Annu. Rev. Genomics Hum. Genet.* 10, 241-262 (2009).
36. Cheong, C. Y. et al. Germline and somatic imprinting in the nonhuman primate highlights species differences in oocyte methylation. *Genome Res.* 25, 611-623 (2015).
37. Xie, W. et al. Base-Resolution Analyses of Sequence and Parent-of-Origin Dependent DNA Methylation in the Mouse Genome. *Cell* 148, 816-831 (2012).
38. Shafin, K. et al. Haplotype-aware variant calling with PEPPER-Margin-DeepVariant enables high accuracy in nanopore long-reads. *Nat. Methods* 18, 1322-1332 (2021).
39. Porubsky, D. et al. Haplotype-resolved inversion landscape reveals hotspots of mutational recurrence associated with genomic disorders. *bioRxiv* 2021.12.20.472354 (2021) doi:10.1101/2021.12.20.472354.
40. Hanlon, V. C. T. et al. Construction of Strand-seq libraries in open nanoliter arrays. *Cell Reports Methods* 2, 100150 (2022).
41. Ledford, H. Cancer geneticists tackle troubling ethnic bias in studies. *Nature* 154-155 (2019) doi:10.1038/d41586-019-01080-2. PMID: 30967668.
42. Shafin, K. et al. Nanopore sequencing and the Shasta toolkit enable efficient de novo assembly of eleven human genomes. *Nat. Biotechnol.* (2020) doi:10.1038/s41587-020-0503-6.
43. Jain, M. et al. Nanopore sequencing and assembly of a human genome with ultra-long reads. *Nat. Biotechnol.* 36, 338-345 (2018).
44. De Coster, W. et al. Structural variants identified by Oxford Nanopore PromethION sequencing of the human genome. *Genome Res.* 29, 1178-1187 (2019).
45. Li, H. Minimap2: pairwise alignment for nucleotide sequences. *Bioinformatics* 34, 3094-3100 (2018).
46. Akbari, V. et al. NanoMethPhase. *Zenodo* (2021) doi: 10.5281/zenodo.4474430.
47. Wagner, J. et al. Benchmarking challenging small variants with linked and long reads. *bioRxiv* 2020.07.24.212712 (2021) doi:10.1101/2020.07.24.212712.
48. Martin, M. Cutadapt removes adapter sequences from high-throughput sequencing reads. *EMBnet.journal*; Vol 17, No 1 *Next Gener. Seq. Data Anal.*—10.14806/ej.17.1.200 (2011).
49. Langmead, B. & Salzberg, S. L. Fast gapped-read alignment with Bowtie 2. *Nat. Methods* 9, 357-359 (2012).
50. Gros, C., Sanders, A. D., Korbel, J. O., Marschall, T. & Ebert, P. ASHLEYS: automated quality control for single-cell Strand-seq data. *Bioinformatics* 37, 3356-3357 (2021).
51. Hanlon, V. C. T., Mattsson, C.-A., Spierings, D. C. J., Guryev, V. & Lansdorp, P. M. InvertypeR: Bayesian inversion genotyping with Strand-seq data. *BMC Genomics* 22, 582 (2021).
52. Stunnenberg, H. G. et al. The International Human Epigenome Consortium: A Blueprint for Scientific Collaboration and Discovery. *Cell* (2016) doi:10.1016/j.cell.2016.11.007.
53. Consortium, E. P. An integrated encyclopedia of DNA elements in the human genome. *Nature* 489, 57 (2012).
54. Bernstein, B. E. et al. The NIH Roadmap Epigenomics Mapping Consortium. *Nat. Biotechnol.* 28, 1045-1048 (2010).
55. Byrska-Bishop, M. et al. High coverage whole genome sequencing of the expanded 1000 Genomes Project cohort including 602 trios. *bioRxiv* 2021.02.06.430068 (2021) doi:10.1101/2021.02.06.430068.
56. Hao, Z. et al. RIdeogram: drawing SVG graphics to visualize and map genome-wide data on the idiograms. *Peer J Comput. Sci.* 6, e251 (2020).
57. Murphy, N. M. et al. Haplotyping the human leukocyte antigen system from single chromosomes. *Sci Rep* 6, 30381 (2016). https://doi.org/10.1038/srep30381.
58. Ramagopalan et al. Parent-of-origin of HLA-DRB1*1501 and age of onset of multiple sclerosis." Journal of Human Genetics 54 (2009): 547-549.
59. Deighton and Walker. The familial nature of rheumatoid arthritis. Annals of the Rheumatic Diseases 1991, 50:62-65.
60. Naranbhai V. et al. HLA-A*03 and response to immune checkpoint blockade in cancer: an epidemiological biomarker study. Lancet Oncol. 2022 January; 23(1):172-184. doi: 10.1016/S1470-2045(21)00582-9. Epub 2021 Dec. 9.
61. de la Cruz, M. R. et al. Cis-acting factors causing secondary epimutations; impact on the risk for cancer and other diseases. Cancers (Basel). 2021 October; 13(19): 4807. Published online 2021 Sep. 26. doi: 10.3390/cancers13194807.
62. Hitchins, M. P. et al. Dominantly inherited constitutional epigenetic silencing of MLH1 in a cancer-affected family is linked to a single nucleotide variant within the 5'UTR. Cancer Cell. 2011 Aug. 16; 20(2):200-13. doi: 10.1016/j.ccr.2011.07.003.
63. Chan, T. et al. Heritable germline epimutation of MSH2 in a family with hereditary nonpolyposis colorectal cancer. Nat Genet 38, 1178-1183 (2006). https://doi.org/10.1038/ng1866.
64. Evans D. G. R. et al. A Dominantly Inherited 5' UTR Variant Causing Methylation-Associated Silencing of BRCA1 as a Cause of Breast and Ovarian Cancer. Am J Hum Genet. 2018 Aug. 2; 103(2):213-220. doi: 10.1016/j.ajhg.2018.07.002. PMID: 30075112; PMCID: PMC6080768.
65. Dixon K. et al. Defining the heterogeneity of unbalanced structural variation underlying breast cancer susceptibility by nanopore genome sequencing. Eur J Hum Genet. 2023 Feb. 16. doi: 10.1038/s41431-023-01284-1. Epub ahead of print. PMID: 36797466.
66. Thibodeau, M. L., et al. Improved structural variant interpretation for hereditary cancer susceptibility using long-read sequencing. Genet Med. 2020 November; 22(11):1892-1897. doi: 10.1038/s41436-020-0880-8. Epub 2020 Jul. 6. PMID: 32624572; PMCID: PMC7605438.
67. Weinberg, C.R. Methods for detection of parent-of-origin effects in genetic studies of case-parents triads. Am J Hum Genet. 1999 July; 65(1): 229-235. doi: 10.1086/302466.
68. Baysal, B. E. et al. Mutations in SDHD, a mitochondrial complex II gene, in hereditary paraganglioma. Science. Feb. 4 2000; 287(5454):848-51. doi:10.1126/science.287.5454.848.
69. Bayley J.P. et al. Paraganglioma and pheochromocytoma upon maternal transmission of SDHD mutations. BMC Med Genet. Oct. 10 2014; 15:111. doi:10.1186/s12881-014-0111-8.
70. Hampel H. et al. Assessment of Tumor Sequencing as a Replacement for Lynch Syndrome Screening and Current Molecular Tests for Patients With Colorectal Cancer. JAMA Oncol. 06 2018; 4(6):806-813. doi:10.1001/jamaoncol.2018.0104.
71. Beard V. K. et al. Genetic testing in families with hereditary colorectal cancer in British Columbia and Yukon: a retrospective cross-sectional analysis. CMAJ Open. 2020 October-December 2020; 8(4):E637-E642. doi:10.9778/cmajo.20190167.
72. LaDuca H. et al. A clinical guide to hereditary cancer panel testing: evaluation of gene-specific cancer associations and sensitivity of genetic testing criteria in a cohort of 165,000 high-risk patients. Genet Med. February 2020; 22(2):407-415. doi:10.1038/s41436-019-0633-8.
73. Schrader K. A., et al. Germline Variants in Targeted Tumor Sequencing Using Matched Normal DNA. JAMA Oncology. 2016; 2(1):104-111. doi:10.1001/jamaoncol.2015.5208.
74. Frey M. K., et al. Prospective Feasibility Trial of a Novel Strategy of Facilitated Cascade Genetic Testing Using Telephone Counseling. J Clin Oncol. May 1 2020; 38(13): 1389-1397. doi:10.1200/jco.19.02005.

The invention claimed is:
1. A method of assigning a parent-of-origin to a chromosome-length haplotype, or of assigning parent-of-origin to one or more alleles contained within the chromosome-length haplotype, for a genome of a subject, the method comprising;
generating chromosome-length haplotypes for each autosomal chromosome of the genome of the subject by:
(i) conducting a first sequencing method that enables determination of long-range phase information;
(ii) conducting a second sequencing method that enables accurate determination and assignment of at least short reads of sequence to a haplotype; and
(iii) using overlapping results of the first and second sequencing methods to generate the chromosome-length haplotypes; and
(iv) determining a methylation status of at least one differentially methylated region (iDMR) associated with each one of the autosomal chromosomes; and
(v) using the determined methylation status of the at least one iDMR associated with each autosomal chromosome to assign a parent-of-origin for each one of the corresponding chromosome-length haplotypes, or to assign a parent of origin to the one or more alleles contained within the corresponding chromosome-length haplotype, based on the determined methylation status of the at least one iDMR associated with each autosomal chromosome.
2. The method of claim 1, wherein results of the first and second sequencing methods conducted at steps (i) and (ii) are used iteratively to phase variants at step (iii), wherein the variants optionally comprise single nucleotide polymorphisms (SNPs) and/or indels.
3. The method of claim 1, wherein step (iv) is conducted concurrently with step (ii) using the second sequencing method.
4. The method of claim 1, wherein the first sequencing method 4 comprises Strand-seq, Hi-C, 3C-Seq, linked-read sequencing, continuous long-read, high-fidelity, Pore-C, or a combination thereof.
5. The method of claim 1, wherein the second sequencing method comprises nanopore sequencing, single-molecule real-time sequencing, bisulfite sequencing, or a combination thereof.
6. The method of claim 1, wherein the first sequencing method and the second sequencing method are the same sequencing method.
7. The method of claim 1, wherein the first sequencing method comprises StrandSeq and the second sequencing method comprises nanopore sequencing, wherein data obtained from the nanopore sequencing is used to call variants, and wherein at least some of the variants are phased with Strand-seq in an inversion aware manner to construct sparse chromosome-length haplotypes.

* * * * *